(12) United States Patent
Lopez

(10) Patent No.: US 11,659,857 B2
(45) Date of Patent: May 30, 2023

(54) CANNABINOID FORMULATIONS FOR AEROSOL DEVICES AND METHODS THEREOF

(71) Applicant: MARKHAM BIOTECH INC., Gormley (CA)

(72) Inventor: John Emilio Lopez, Gormley (CA)

(73) Assignee: MARKHAM BIOTECH, INC., Gormley (CA)

( * ) Notice: Subject to any disclaimer, the term of this patent is extended or adjusted under 35 U.S.C. 154(b) by 240 days.

(21) Appl. No.: 17/155,635

(22) Filed: Jan. 22, 2021

(65) Prior Publication Data

US 2021/0337856 A1 Nov. 4, 2021

Related U.S. Application Data

(63) Continuation of application No. 15/942,174, filed on Mar. 30, 2018, now Pat. No. 10,932,497.

(60) Provisional application No. 62/479,194, filed on Mar. 30, 2017.

(51) Int. Cl.
| | |
|---|---|
| A24F 47/00 | (2020.01) |
| A24B 15/167 | (2020.01) |
| A61K 31/00 | (2006.01) |
| A61K 31/05 | (2006.01) |
| C07B 63/00 | (2006.01) |
| C07D 311/80 | (2006.01) |
| A24F 40/10 | (2020.01) |

(52) U.S. Cl.
CPC ............ *A24B 15/167* (2016.11); *A61K 31/00* (2013.01); *A61K 31/05* (2013.01); *A24F 40/10* (2020.01); *C07B 63/00* (2013.01); *C07D 311/80* (2013.01)

(58) Field of Classification Search
CPC .............................. A24B 15/167; A24F 40/10
See application file for complete search history.

(56) References Cited

U.S. PATENT DOCUMENTS

| | | | | |
|---|---|---|---|---|
| 2013/0220315 A1* | 8/2013 | Conley | ................ | A61M 11/042 128/202.21 |
| 2014/0209109 A1* | 7/2014 | Larson | ................. | A61K 31/352 131/329 |
| 2014/0345631 A1* | 11/2014 | Bowen | .................. | A61K 31/60 131/328 |
| 2015/0083146 A1* | 3/2015 | Goldman | ............. | A61K 31/352 131/352 |
| 2015/0128972 A1* | 5/2015 | Verleur | ................. | H02J 7/0042 131/329 |
| 2015/0181924 A1* | 7/2015 | Llamas | ................ | A24B 15/167 131/369 |
| 2015/0208729 A1* | 7/2015 | Monsees | ............... | H02J 7/0034 131/329 |
| 2016/0151328 A1* | 6/2016 | Doane | .................... | A61Q 19/00 514/454 |
| 2016/0271347 A1* | 9/2016 | Raich | ....................... | A24F 40/42 |
| 2016/0309774 A1* | 10/2016 | Wand | .................... | A61K 31/455 |
| 2016/0325055 A1* | 11/2016 | Cameron | ................ | A24F 40/50 |
| 2017/0055588 A1* | 3/2017 | Cameron | ............. | A61M 15/06 |
| 2017/0251726 A1* | 9/2017 | Nielsen | ................... | A24F 40/40 |
| 2017/0259170 A1* | 9/2017 | Bowen | ................... | A24F 40/60 |

(Continued)

*Primary Examiner* — Eric Yaary
(74) *Attorney, Agent, or Firm* — McDonnell Boehnen Hulbert & Berghoff LLP

(57) ABSTRACT

The disclosure provides methods, formulations, and apparatus for making and using cannabinoid formulations.

20 Claims, 8 Drawing Sheets

(56) References Cited

U.S. PATENT DOCUMENTS

2018/0043114 A1\* 2/2018 Bowen .................... A24F 40/60
2018/0243259 A1\* 8/2018 Nguyen ............... A61K 36/185

\* cited by examiner

CANNABINOID FORMULATIONS FOR AEROSOL DEVICES AND METHODS THEREOF

CROSS-REFERENCE TO RELATED APPLICATIONS

This patent application claims the benefit of priority of U.S. patent application Ser. No. 15/942,174 filed on Mar. 30, 2018 and U.S. Provisional Patent Application No. 62/479,194, filed Mar. 30, 2017, incorporated herein by reference in their entireties.

BACKGROUND

Field of the Invention

The disclosure provides methods, formulations, and apparatus for making and using cannabinoid formulations.

Description of Related Art

Cannabinoids are chemical compounds and increase the heart rate when administered to an animal or individual. Cannabinoid transfer to an individual has been studied extensively, and research has substantiated that cannabinoids are medically beneficial in the treatment of anorexia, insomnia, nausea, pain relief, and associated with a feeling of physical and/or emotional satisfaction, in individuals. Cannabinoid administration decreased subjective ratings of pain in neuropathic populations, using a laboratory model of pain that has predictive validity for clinical efficacy of analgesics in non-pain populations. Some reports have posited that vaporized or aerosolized administrations are preferred due to the faster onset and shorter duration of action, reduced exposure to harmful pyrolytic compounds, and the ability for patients to titrate dosage to the desired effect. One non-limiting example of a known shortcoming of the traditional cannabis cigarette is exposure to tar. Cannabinoid vaporization and/or aerosolized administration is a new technique that avoids the production of irritating respiratory toxins by heating the cannabinoid formulation, described herein, to a temperature where active cannabinoid vapors form, but below the point of combustion where toxins are released.

SUMMARY OF THE INVENTION

In certain embodiments, the disclosure provides cannabinoid liquid formulations comprising a cannabinoid extract, wherein the cannabinoid extract comprises one or more cannabinoids dissolved in a solvent; and a biologically acceptable liquid carrier comprised of glycerol, vegetable glycerin, propylene glycol, trimethylene glycol, water, or ethanol. In further embodiments, the disclosure provides cannabinoid liquid formulations wherein the liquid carrier comprises propylene glycol and vegetable glycerin. In certain embodiments, the disclosure provides cannabinoid liquid formulations wherein liquid carrier comprises between 80% and 50% propylene glycol, and between 20% and 50% vegetable glycerin. In some embodiments, the disclosure provides cannabinoid liquid formulations wherein the liquid carrier comprises 70% propylene glycol and 30% vegetable glycerin, or 80% propylene glycol and 20% vegetable glycerin.

In certain embodiments, the disclosure provides cannabinoid liquid formulations comprising a cannabinoid extract, wherein the cannabinoid extract comprises one or more cannabinoids dissolved in a solvent, and wherein the solvent is characterized by a vapor pressure less than 25 bar at 50° C. In other embodiments, the solvent is characterized by vapor pressure of 10 to 10,000 bar at 25° C. In embodiments, the solvent is $CO_2$, methane, ethane, propane, butane, pentane, hexane, heptane, octane, nonane, decane, undecane, dodecane, tridecane, tetradecane, pentadecane, hexadecane, heptadecane, octadecane, nonadecane, or eicosane. In particular embodiments, the solvent is propane, butane, or pentane.

In certain embodiments, the disclosure provides cannabinoid liquid formulations comprising cannabinoids, wherein the liquid formulation has a cannabinoid concentration of about 1% (w/w) to about 50% (w/w), about 1% (w/w) to about 35% (w/w), about 4% (w/w) to about 25% (w/w), about 4% (w/w) to about 15% (w/w), about 0.5% (w/w) to about 10% (w/w), about 0.5% (w/w) to about 5% (w/w), or about 0.5% (w/w) to about 1% (w/w). In particular embodiments, the liquid formulation has a cannabinoid concentration of about 5% (w/w) to about 10% (w/w).

In certain embodiments, the disclosure provides cannabinoid liquid formulations, and further comprising one or more flavorants.

In certain embodiments of the liquid formulation of the disclosure, one or more cannabinoids are synthetic, and have a purity of greater than about 80% pure, greater than about 85% pure, greater than about 90% pure, greater than about 95% pure, or greater than about 99% pure.

Certain embodiments of the disclosure also provide an electronic cigarette for delivering inhalable aerosol comprising, a fluid storage compartment, a cannabinoid liquid formulation disposed within the fluid storage compartment, a heater, a battery, and a mouthpiece.

In certain embodiments, the liquid formulation comprises a solvent with a melting point at least 20 degrees lower than an operating temperature of the electronic cigarette, a boiling point no more than 300 degrees lower than the operating temperature of the electronic cigarette, and at least a 15-degree difference between the melting point and the boiling point.

In certain embodiments, the liquid formulation comprises a solvent with a melting point less than 55 C, a boiling point greater than −165 C, and at least a 15-degree difference between the melting point and the boiling point.

In certain embodiments, the heater of the electronic cigarette the disclosure has an operating temperature between 150 C and 250 C, or between 180 C and 220 C. In some embodiments, the heater of the electronic cigarette has an operating temperature of 200 C.

Certain embodiments of the disclosure also provide a cartomizer for an electronic cigarette comprising a cannabinoid liquid formulation comprising a cannabinoid extract and a biologically acceptable liquid carrier, a fluid storage compartment, and an atomizer comprising a heating element in fluid communication with the cannabinoid liquid formulation.

Certain embodiments s of the disclosure also provide a cartridge for use in an electronic cigarette comprising a cannabinoid liquid formulation comprising a cannabinoid extract and a biologically acceptable liquid carrier.

In certain embodiments, the disclosure provides a kit comprising an electronic cigarette for generating an inhalable aerosol, a cartridge containing a cannabinoid liquid formulation comprising, wherein the liquid formulation is a cannabinoid extract in a biologically acceptable liquid carrier; and instructions for using the electronic cigarette to generate an inhalable aerosol.

The disclosure also provides a method of preparing a liquid cannabinoid formulation comprising, introducing a suitable organic solvent to a cannabis plant or part thereof to form a neat mixture comprising a cannabinoid extract, purging the organic solvent out of the neat mixture at ambient or elevated temperature to form a purged cannabinoid extract, and diluting the purged cannabinoid extract with a mixture of propylene glycol and glycerin. In certain embodiments of the method, the organic solvent is completely purged from the cannabinoid extract prior to diluting with the carrier mixture. In some embodiments, the mixture of propylene glycol and glycerin comprises a solution of 8:2 or 3:7 ratio by weight of propylene glycol and vegetable glycerin. In some embodiments, the method of preparing a liquid cannabinoid formulation of the disclosure further comprising adding one or more exogenous flavorants. In embodiments, the method of preparing the liquid cannabinoid formulation results in a formulation with two or more cannabinoids.

In some embodiments, the disclosure provides a method of administering cannabinoids comprising, heating a cannabinoid liquid formulation of the disclosure to generate an inhalable aerosol comprising one or more cannabinoids, and inhaling the aerosol. In certain embodiments, the method of administering cannabinoids comprises heating a liquid cannabinoid formulation of the disclosure with an electronic cigarette operated at between 150 C and 250 C, or between 180 C and 220 C. In embodiments, the methods of the disclosure generates an inhalable aerosol comprising a condensate of one or more cannabinoids, wherein the condensate comprises particle sizes from about 0.1 microns to about 5 microns, from about 0.1 microns to about 1 or 2 microns, from about 0.1 microns to about 0.7 microns, or from about 0.3 microns to about 0.4 microns. In embodiments, the method of the disclosure generates an inhalable aerosol that comprises about 1% to about 50% (w/w) cannabinoid.

In embodiments, the method of administering cannabinoids disclosed herein results in a maximum blood cannabinoid concentration ($C_{max)\ over}$ 10 ng/mL, between 10 ng/mL and 16 ng/mL, between 11 ng/mL and 15 ng/mL, or between 11 ng/mL and 14 ng/mL.

In embodiments, the method of administering cannabinoids disclosed herein results in a time at which the maximum concentration of cannabinoid is measured in the blood ($T_{max}$) of under 25 minutes, under 20 minutes, under 15 minutes, or under 10 minutes. In some embodiments, the method of administering cannabinoids disclosed herein results in a time at which the maximum concentration of cannabinoid is measured in the blood ($T_{max}$) of between 3 minutes to 7.5 minutes.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description can be best understood when read in conjunction with the following drawings in which.

DETAILED DESCRIPTION OF THE INVENTION

Figure 1:
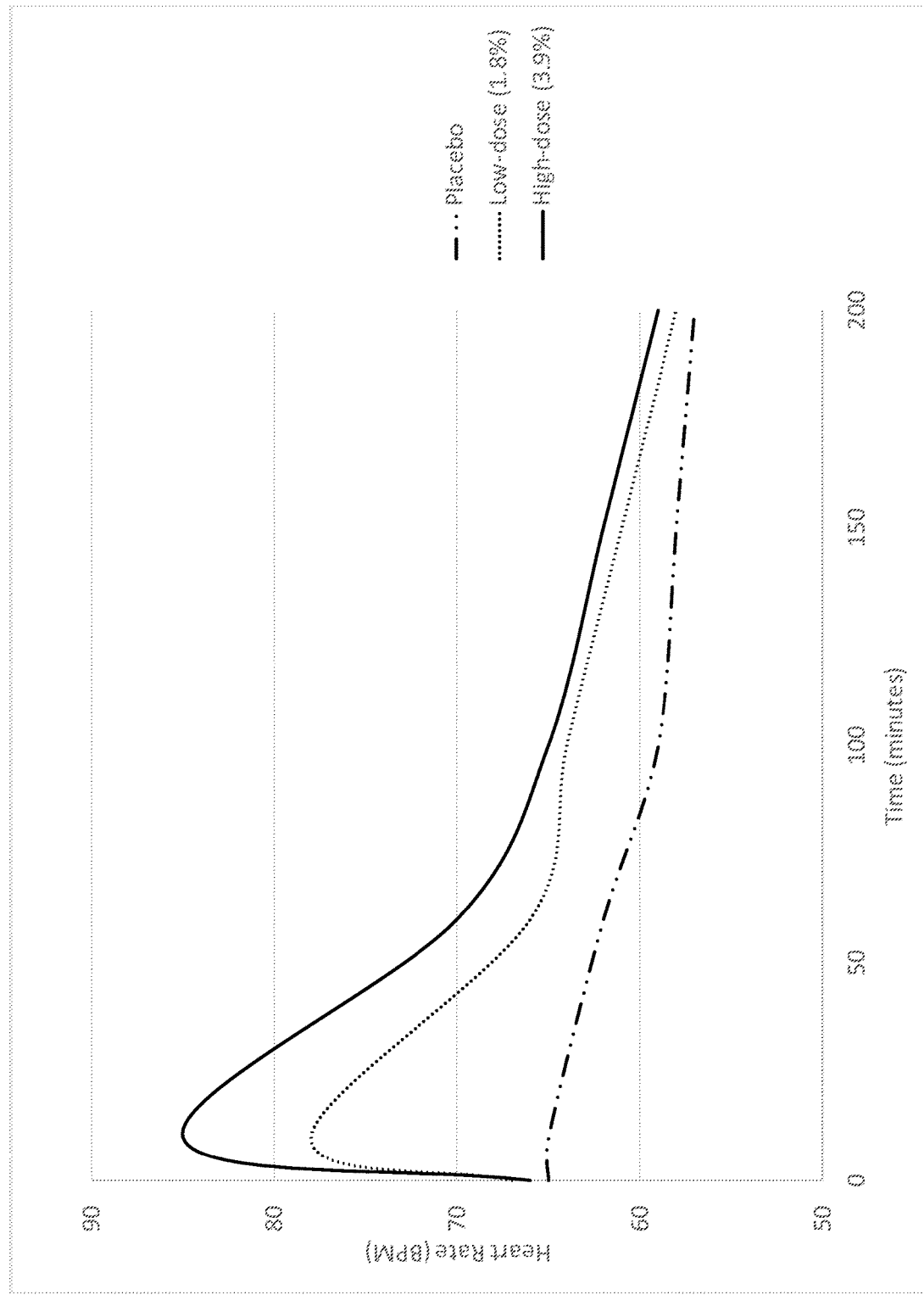
FIG. 1 illustrates results of heart rate data measured for 200 minutes from start of puffing. Y-axis is heart rate (bpm) and X-axis represent duration of the test (0 to 200 minutes)

Certain embodiments of the disclosure provide cannabinoid formulations with pain relief and therapeutic benefits superior to that of oral cannabinoid administration, and more comparable to the pain relief in an individual smoking a traditional cannabis cigarette. In embodiments, the disclosure provides efficient transfer of cannabinoid to the lungs of an individual and a rapid rise of cannabinoid absorption in the plasma as shown, for non-limiting example, in Example 8. In some embodiments, the disclosure provides cannabinoid formulations with unexpected pain relief effects, and greater satisfaction for users, than other cannabinoid formulations. For example, embodiments of the disclosure provide unexpected results associated with blood plasma levels achieved with the cannabinoid formulations herein. In certain embodiments, the disclosure provides methods and formulations that achieve advantageous improvements in cannabinoid uptake in the blood relative to previous methods and formulations, such as higher uptake from the present cannabinoid formulations aerosolized by an electronic cigarette. Therefore, described herein are cannabinoid formulations for use in an electronic cigarette, or comparable devices, that provide a general pain relief effect, therapeutic benefit, and/or satisfaction consistent with an efficient transfer of cannabinoid to the lungs of an individual and a rapid rise of cannabinoid absorption in the plasma. In embodiments, the disclosure provides devices, formulation of cannabinoid, systems, cartomizers, kits and methods that are used to inhale an aerosol generated from a cannabinoid liquid formulation through the mouth or nose as described herein or as would be obvious to one of skill in the art upon reading the disclosure herein.

Provided herein is a method of delivering cannabinoid to a user comprising operating an aerosol inhalation device, also known as "electronic cigarette" to a user wherein the electronic cigarette comprises a cannabinoid formulation comprising a cannabinoid in a biologically acceptable liquid carrier wherein an organic solvent used to form said cannabinoids are characterized by vapor pressure <25 bar at 50° C., and inhaling an aerosol generated from the cannabinoid formulation heated by the electronic cigarette.

Provided herein is a method of delivering cannabinoid to a user comprising operating an electronic cigarette to a user wherein the electronic cigarette comprises a cannabinoid formulation comprising a cannabinoid in a biologically acceptable liquid carrier wherein an organic solvent used to form said cannabinoids are characterized by vapor pressure of about 100 to 10,000 bar at 25° C., and inhaling an aerosol generated from the cannabinoid formulation heated by the electronic cigarette.

Provided herein is a method of delivering cannabinoid to a user comprising operating an electronic cigarette wherein the electronic cigarette comprises a cannabinoid formulation comprising a cannabinoid in a biologically acceptable liquid carrier wherein an organic solvent used to form said cannabinoids are further characterized by a melting point <55° C., a boiling point >-165° C., and at least a 15-degree difference between the melting point and the boiling point, and inhaling an aerosol generated from the cannabinoid formulation heated by the electronic cigarette.

Provided herein is a method of delivering cannabinoids to a user comprising providing an electronic cigarette to a user wherein the electronic cigarette comprises a cannabinoid formulation comprising a cannabinoid in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 15-degree difference between the melting point and the boiling point, and inhaling an aerosol generated from the cannabinoid formulation heated by the electronic cigarette. In embodiments, operating temperature of the electronic cigarette is from 150° C. to 250° C. In other embodiments, operating temperature of the electronic cigarette is from 180° C. to 220° C. In still other embodiments, the operating temperature of the electronic cigarette is about 200° C.

Certain embodiments of the methods provided herein comprise delivering cannabinoids to the blood of a user, said methods comprising providing an aerosol that is inhaled by the user from an electronic cigarette that comprises a cannabinoid formulation wherein providing the aerosol comprises the electronic cigarette heating the formulation thereby generating the aerosol, wherein the aerosol is effective in delivering a level of cannabinoid in the blood of the user that is at least 0.20 ng/mL at about 1.5 minutes after a first puff of ten puffs of the aerosol, each puff taken at 30 second intervals. In certain embodiments the aerosol comprises a condensate of cannabinoid. In embodiments the aerosol comprises condensate of multiple cannabinoids. In embodiments the aerosol comprises condensate of cannabinoid and condensate of the carrier. In certain embodiments the aerosol comprises condensate of cannabinoid and condensate of the organic solvent. In embodiments the aerosol comprises condensate in particle sizes from about 0.1 microns to about 5 microns. In embodiments the aerosol comprises condensate in particle sizes from about 0.1 microns to about 1 or 2 microns. In certain embodiments the aerosol comprises condensate in particle sizes from about 0.1 microns to about 0.7 microns. In embodiments the aerosol comprises condensate in particle sizes from about 0.3 microns to about 0.4 microns.

In certain embodiments, the methods provided herein result in a maximum blood cannabinoid concentration ($C_{max}$) over 10 ng/mL, or over 11 ng/mL. between 10 ng/mL and 16 ng/mL between 11 ng/mL and 15 ng/mL on average. In certain embodiments, the methods provided herein result in a maximum blood cannabinoid concentration ($C_{max}$) between 10 ng/mL and 16 ng/mL, is between 11 ng/mL and 15 ng/mL, or between 11 ng/mL and 14 ng/mL.

In certain embodiments s of the method herein, inhaling the aerosol results in a time at which the maximum concentration of cannabinoid is measured in the blood (Tmax) of under 25 minutes, under 20 minutes, under 15 minutes, or under 10 minutes. In some embodiments, inhaling the aerosol results in a time at which the maximum concentration of cannabinoid is measured (Tmax) of from 3 minutes to 15 minutes, or from 3 minutes to 7.5 minutes.

In certain embodiments, the heating of the formulation is at a temperature from 75° C. to 325° C., a temperature from 180° C. to 220° C., or a temperature of about 200° C.

Provided herein is a cannabinoid liquid formulation in an electronic cigarette for generating an inhalable aerosol upon heating in the electronic cigarette, the formulation in the cigarette comprising a cannabinoid in a biologically acceptable liquid carrier wherein an organic solvent used to form said cannabinoids are characterized by vapor pressure <25 bar at 50° C.

Provided herein is a cannabinoid liquid formulation in an electronic cigarette for generating an inhalable aerosol upon heating in the electronic cigarette, the formulation in the cigarette comprising a cannabinoid in a biologically acceptable liquid carrier wherein an organic solvent used to form said cannabinoids are characterized by vapor pressure of about 100 to 10,000 bar at 25° C.

Provided herein is a cannabinoid liquid formulation in an electronic cigarette for generating an inhalable aerosol upon heating in the electronic cigarette, the formulation in the cigarette comprising a cannabinoid in a biologically acceptable liquid carrier wherein an organic solvent used to form said cannabinoids are further characterized by a melting point <55° C., a boiling point >-165° C., and at least a 15-degree difference between the melting point and the boiling point.

Provided herein is a cannabinoid liquid formulation in an electronic cigarette for generating an inhalable aerosol upon heating in the electronic cigarette, the formulation in the cigarette comprising a cannabinoid in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 15-degree difference between the melting point and the boiling point.

Provided herein is a cannabinoid liquid formulation for generating an inhalable aerosol upon heating in the electronic cigarette, the cannabinoid liquid formulation comprising a cannabinoid in a biologically acceptable liquid carrier wherein an organic solvent used to form said cannabinoids are characterized by vapor pressure <25 bar at 50° C.

Provided herein is a cannabinoid liquid formulation for generating an inhalable aerosol upon heating in the electronic cigarette, the cannabinoid liquid formulation comprising a cannabinoid in a biologically acceptable liquid carrier wherein an organic solvent used to form said cannabinoids are characterized by vapor pressure of about 100 to 10,000 bar at 25° C.

Provided herein is a cannabinoid liquid formulation for generating an inhalable aerosol upon heating in the electronic cigarette, the cannabinoid liquid formulation comprising a cannabinoid in a biologically acceptable liquid carrier wherein an organic solvent used to form said cannabinoids are further characterized by a melting point <160° C., a boiling point >-165° C., and at least a 15-degree difference between the melting point and the boiling point.

Provided herein is a cannabinoid liquid formulation for generating an inhalable aerosol upon heating in the electronic cigarette, the cannabinoid liquid formulation comprising a cannabinoid in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 15-degree difference between the melting point and the boiling point.

Provided herein is a cannabinoid liquid formulation for use in an electronic cigarette the cannabinoid liquid formulation comprising a cannabinoid in a biologically acceptable liquid carrier wherein an organic solvent used to form said cannabinoids are characterized by vapor pressure <25 bar at 50° C.

Provided herein is a cannabinoid liquid formulation for use in an electronic cigarette the cannabinoid liquid formulation comprising a cannabinoid in a biologically acceptable liquid carrier wherein an organic solvent used to form said cannabinoids are characterized by vapor pressure of about 100 to 10,000 bar at 25° C.

Provided herein is a cannabinoid liquid formulation for use in an electronic cigarette the cannabinoid liquid formulation comprising a cannabinoid in a biologically acceptable liquid carrier wherein an organic solvent used to form said cannabinoids are further characterized by a melting point <55° C., a boiling point >−165° C., and at least a 15-degree difference between the melting point and the boiling point.

Provided herein is a cannabinoid liquid formulation for use in an electronic cigarette the cannabinoid liquid formulation comprising a cannabinoid in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 15-degree difference between the melting point and the boiling point.

Provided herein is a use of a cannabinoid formulation for delivery of cannabinoid to a user from an electronic cigarette wherein the cannabinoid formulation comprises a cannabinoid in a biologically acceptable liquid carrier wherein an organic solvent used to form said cannabinoids are characterized by vapor pressure <25 bar at 50° C., and the cannabinoid formulation is heated by the electronic cigarette to generate an aerosol inhalable by the user.

Provided herein is a use of a cannabinoid formulation for delivery of cannabinoid to a user from an electronic cigarette wherein the cannabinoid formulation comprises a cannabinoid in a biologically acceptable liquid carrier wherein an organic solvent used to form said cannabinoids are characterized by vapor pressure of about 100 to 10,000 bar at 25° C., and the cannabinoid formulation is heated by the electronic cigarette to generate an aerosol inhalable by the user.

Provided herein is a use of a cannabinoid formulation for delivery of cannabinoid to a user from an electronic cigarette wherein the cannabinoid formulation comprises a cannabinoid in a biologically acceptable liquid carrier wherein an organic solvent used to form said cannabinoids are further characterized by a melting point <55° C., a boiling point >−165° C., and at least a 15-degree difference between the melting point and the boiling point, and the cannabinoid formulation is heated by the electronic cigarette to generate an aerosol inhalable by the user.

Provided herein is a use of a cannabinoid formulation for delivery of cannabinoid to the blood of a user from an electronic cigarette, wherein the cannabinoid formulation in the electronic cigarette is heated to form an aerosol which delivers a level of cannabinoid in the blood of the user that is at least 0.20 ng/mL at about 1.5 minutes after a first puff of ten puffs of the aerosol, each puff taken at 30 second intervals.

Provided herein is a use of a cannabinoid formulation for delivery of cannabinoid to a user from an electronic cigarette wherein the cannabinoid formulation comprises a cannabinoid salt in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 15-degree difference between the melting point and the boiling point, and the cannabinoid formulation is heated by the electronic cigarette to generate an aerosol inhalable by the user.

In certain embodiments, the cannabinoid formulation comprises a cannabinoid in a biologically acceptable liquid carrier wherein an organic solvent used to form said cannabinoid is further characterized by a melting point at least 20 degrees lower than the operating temperature of the electronic cigarette, a boiling point no more than 300 degrees lower than the operating temperature of the electronic cigarette, and at least a 15-degree difference between the melting point and the boiling point; and the operating temperature is 200° C.

Provided herein is a cartomizer for an electronic cigarette comprising:
  a cannabinoid liquid formulation comprising a cannabinoid in a biologically acceptable liquid carrier wherein an organic solvent used to form said cannabinoids are characterized by vapor pressure <25 bar at 50° C.;
  an atomizer comprising a heating element in fluid communication with the cannabinoid liquid formulation; and
  a fluid storage compartment that stores the cannabinoid liquid formulation.

Provided herein is a cartomizer for an electronic cigarette comprising:
  a cannabinoid liquid formulation comprising a cannabinoid in a biologically acceptable liquid carrier wherein an organic solvent used to form said cannabinoids are characterized by vapor pressure of about 100 to 10,000 bar at 25° C.;
  an atomizer comprising a heating element in fluid communication with the cannabinoid liquid formulation; and
  a fluid storage compartment that stores the cannabinoid liquid formulation.

Provided herein is a cartomizer for an electronic cigarette comprising:
  a cannabinoid liquid formulation comprising a cannabinoid in a biologically acceptable liquid carrier wherein an organic solvent used to form said cannabinoids are further characterized by a melting point <55° C., a boiling point >−165° C., and at least a 15-degree difference between the melting point and the boiling point;
  an atomizer comprising a heating element in fluid communication with the cannabinoid liquid formulation; and
  a fluid storage compartment that stores the cannabinoid liquid formulation.

Provided herein is a cartomizer for an electronic cigarette comprising:
- a cannabinoid liquid formulation comprising a cannabinoid in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 20-degree difference between the melting point and the boiling point;
- an atomizer comprising a heating element in fluid communication with the cannabinoid liquid formulation; and
- a fluid storage compartment that stores the cannabinoid liquid formulation.

Provided herein is an electronic cigarette for generating an inhalable aerosol comprising:
- a fluid storage compartment;
- a heater; and
- a cannabinoid liquid formulation in the fluid storage compartment, the liquid formulation comprising a cannabinoid in a biologically acceptable liquid carrier wherein an organic solvent used to form said cannabinoids are characterized by vapor pressure <25 bar at 50° C.;
- a battery; and
- a mouthpiece.

Provided herein is an electronic cigarette for generating an inhalable aerosol comprising:
- a fluid storage compartment;
- a heater; and
- a cannabinoid liquid formulation in the fluid storage compartment, the liquid formulation comprising a cannabinoid in a biologically acceptable liquid carrier wherein an organic solvent used to form said cannabinoids are characterized by vapor pressure of about 100 to 10,000 bar at 25° C.;
- a battery;
- and a mouthpiece.

Provided herein is an electronic cigarette for generating an inhalable aerosol comprising:
- a fluid storage compartment;
- a heater; and
- a cannabinoid liquid formulation in the fluid storage compartment, the liquid formulation comprising a cannabinoid in a biologically acceptable liquid carrier wherein an organic solvent used to form said cannabinoids are further characterized by a melting point <55° C., a boiling point >−165° C., and at least a 15-degree difference between the melting point and the boiling point;
- a battery;
- and a mouthpiece.

Provided herein is an electronic cigarette for generating an inhalable aerosol comprising:
- a fluid storage compartment;
- a heater; and
- a cannabinoid liquid formulation in the fluid storage compartment, the liquid formulation comprising a cannabinoid in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 15-degree difference between the melting point and the boiling point;
- a battery; and a mouthpiece.

Provided herein is a cartridge in an electronic cigarette comprising a fluid storage compartment, wherein the fluid storage compartment stores a cannabinoid liquid formulation comprising a cannabinoid in a biologically acceptable liquid carrier wherein an organic solvent used to form said cannabinoids are characterized by vapor pressure <25 bar at 50° C.

Provided herein is a cartridge in an electronic cigarette comprising a fluid storage compartment, wherein the fluid storage compartment stores a cannabinoid liquid formulation comprising a cannabinoid in a biologically acceptable liquid carrier wherein an organic solvent used to form said cannabinoids are characterized by vapor pressure of about 100 to 10,000 bar at 25° C.

Provided herein is a cartridge in an electronic cigarette comprising a fluid storage compartment, wherein the fluid storage compartment stores a cannabinoid liquid formulation comprising a cannabinoid in a biologically acceptable liquid carrier wherein an organic solvent used to form said cannabinoids are further characterized by a melting point <55° C., a boiling point >−165° C., and at least a 15-degree difference between the melting point and the boiling point.

Provided herein is a cartridge in an electronic cigarette comprising a fluid storage compartment, wherein the fluid storage compartment stores a cannabinoid liquid formulation comprising a cannabinoid in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 15-degree difference between the melting point and the boiling point.

Provided herein is a kit comprising:
(a) an electronic cigarette for generating an inhalable aerosol comprising
  I. a device body comprising a cartridge receptacle;
  II. a cartridge comprising a fluid storage compartment, wherein the fluid storage compartment stores a cannabinoid liquid formulation comprising a cannabinoid in a biologically acceptable liquid carrier wherein an organic solvent used to form said cannabinoids are characterized by vapor pressure <25 bar at 50° C.;
  III. a heater;
  IV. a battery; and
  V. a mouthpiece; and
(b) instructions for using the electronic cigarette to generate an inhalable aerosol.

Provided herein is a kit comprising:
(a) an electronic cigarette for generating an inhalable aerosol comprising
  I. a device body comprising a cartridge receptacle;
  II. a cartridge comprising a fluid storage compartment, wherein the fluid storage compartment stores a cannabinoid liquid formulation comprising a cannabinoid in a biologically acceptable liquid carrier wherein an organic solvent used to form said cannabinoids are characterized by vapor pressure of about 100 to 10,000 bar at 25° C.;
  III. a heater;
  IV. a battery; and
  V. a mouthpiece; and (b) instructions for using the electronic cigarette to generate an inhalable aerosol.

Provided herein is a kit comprising:
(a) an electronic cigarette for generating an inhalable aerosol comprising
  I. a device body comprising a cartridge receptacle;
  II. a cartridge comprising a fluid storage compartment, wherein the fluid storage compartment stores a cannabinoid liquid formulation comprising a cannabinoid in a biologically acceptable liquid carrier wherein an organic solvent used to form said cannabinoids are further characterized by a melting point <55° C., a boiling point >−165° C., and at least a 15-degree difference between the melting point and the boiling point;
  III. a heater;
  IV. a battery; and
  V. a mouthpiece; and
(b) instructions for using the electronic cigarette to generate an inhalable aerosol.

Provided herein is a kit comprising:
(a) an electronic cigarette for generating an inhalable aerosol comprising
  I. a device body comprising a cartridge receptacle;
  II. a cartridge comprising a fluid storage compartment, wherein the fluid storage compartment stores a cannabinoid liquid formulation comprising a cannabinoid in a biologically acceptable liquid carrier wherein an organic solvent used to form said cannabinoids are further characterized by a melting point at least 20 degrees lower than an operating temperature of the electronic cigarette, a boiling point no more than 300 degrees lower than the operating temperature of the electronic cigarette, and at least a 15-degree difference between the melting point and the boiling point;
  III. a heater;
  IV. a battery; and
  V. a mouthpiece; and
(b) instructions for using the electronic cigarette to generate an inhalable aerosol.

As provided herein, it has unexpectedly been found that there is a difference between the $C_{max}$ (maximum concentration) and $T_{max}$ (time at which the maximum concentration is measured) when measuring blood plasma cannabinoid levels of cannabinoid formulations provided herein inhaled using a low temperature vaporization device, i.e. electronic cigarette, as compared to the $C_{max}$ and $T_{max}$ (similarly measuring blood plasma cannabinoid levels) of a traditional cannabis cigarette. Also provided herein, it has unexpectedly been found herein that there is a difference between the $C_{max}$ (maximum concentration) and $T_{max}$ (time at which the maximum concentration is measured) when measuring blood plasma cannabinoid levels of the cannabinoid formulations of the disclosure inhaled using a low temperature vaporization device, i.e. electronic cigarette, as compared to the $C_{max}$ and $T_{max}$ (similarly measuring blood plasma cannabinoid levels) of other known cannabinoid formulations inhaled using a low temperature vaporization device, i.e. electronic cigarette. Additionally, it has unexpectedly been found that there is a difference between the rate of cannabinoid uptake in the plasma of users inhaling cannabinoid formulations provided herein using a low temperature vaporization device, i.e. electronic cigarette, as compared to the rate of cannabinoid uptake in the plasma of users inhaling smoke of a traditional cannabis cigarette. Furthermore, it has unexpectedly been found that there is a difference between the rate of cannabinoid uptake in the plasma of users inhaling cannabinoid formulations provided herein using a low temperature vaporization device, i.e. electronic cigarette, as compared to the rate of cannabinoid uptake in the plasma of users taking other known cannabinoid formulations.

Also consistent with these satisfaction effects, it has unexpectedly been found herein that while there appears to be comparable $C_{max}$ and $T_{max}$ values (measuring blood plasma cannabinoid levels) of cannabinoid formulations inhaled using a low temperature vaporization device, i.e. electronic cigarette, as compared to the $C_{max}$ and $T_{max}$ (similarly measuring blood plasma cannabinoid levels) of a traditional cannabis cigarette, there is a demonstrable difference between the rate of cannabinoid uptake in the plasma of users inhaling certain cannabinoid formulations using a low temperature vaporization device, i.e. electronic cigarette, as compared to the rate of cannabinoid uptake in the plasma of users inhaling other cannabinoid formulations using a low temperature vaporization device, i.e. electronic cigarette. It is also unexpected that while the $C_{max}$ and $T_{max}$ values are comparable to those of a traditional cannabis cigarette, (or are approaching that of a traditional cannabis cigarette), the rate of cannabinoid uptake in the plasma of blood of users is higher in certain cannabinoid formulations than that of the traditional cannabis cigarette. The cannabinoid formulations that demonstrate the quickest rate of cannabinoid uptake in the plasma were more preferred in satisfaction evaluations, and were rated more equivalent to cannabis cigarette satisfaction than the cannabinoid formulations showing the slowest rates of rise of cannabinoid in the subjects' blood plasma. In addition, increasing the concentration of the cannabinoid in the formulation may not necessarily impact the rate of absorption of cannabinoid in the blood (see, for non-limiting example Example 8, cannabinoid formulations tested in 45% and 30% concentrations).

Thus, considering all cannabinoid formulations used in e-cigarettes, some cannabinoid formulations delivered using an e-cigarette appear comparable in $C_{max}$ and $T_{max}$ values (measuring blood plasma cannabinoid levels), however, not all cannabinoids perform similarly to each other or to a traditional cannabis cigarette with respect to the rate of cannabinoid uptake in the blood at early time periods (0-30 minutes). These results are unexpected. Cannabinoid formulations made using organic solvents having a Vapor Pressure between 10 to 10,000 bar @25° C., or Vapor Pressure <25 bar @50° C., or a Vapor Pressure from 10 to 10,000 bar @25° C., or a Vapor Pressure from 100 to 10,000 bar @25° C., a Vapor Pressure between 100 and 10,000 bar @25° C. appear to have a higher rate of cannabinoid uptake in the blood at early time periods (0-5 minutes, 0-10 minutes, 0-15 minutes, 0-30 minutes for non-limiting example) than other cannabinoid formulations, however, they also provide pain relief, therapeutic benefit, and satisfaction comparable to a traditional cannabis cigarette or closer to a traditional cannabis cigarette (as compared to oral cannabinoid formulations or as compared to other cannabinoid formulations). For non-limiting example, organic solvents that meet one or more criteria of the prior sentence include propane, butane, pentane, and $CO_2$. Cannabinoid formulations made using organic solvents that have a difference between boiling point and melting point of at least 15° C., and a boiling point greater than −165° C., and a melting point less than 55° C. appear to have a higher rate of cannabinoid uptake in the blood at early time periods 0-1.5 minutes, 0-2 minutes, 0-3 minutes, 0-4 minutes for non-limiting example) than other cannabinoid formulations, however, they also provide satisfaction comparable to a traditional cigarette or closer to a traditional cigarette (as compared to oral cannabinoid formulations or as compared to other cannabinoid formulations). For non-limiting example, organic solvents that meet the criteria of the prior sentence include propane, butane, pentane, and $CO_2$. Cannabinoid formulations made using organic solvents that have a difference between boiling point and melting point of at least 15° C., and a boiling point at most 300° C. less than operating temperature, and a melting point at least 20° C. lower than operating temperature appear to have a higher rate of cannabinoid uptake in the blood at early time periods 0-1.5 minutes, 0-2 minutes, 0-3 minutes, 0-4 minutes for non-limiting example) than other cannabinoid formulations, however, they also provide satisfaction comparable to a traditional cannabis cigarette or closer to a traditional cannabis cigarette (as compared to oral cannabinoid formulations or as compared to other cannabinoid formulations).

In certain embodiments, the operating temperature is about 75° C. to about 325° C., 100° C. to 300° C., or about 200° C., about 150° C. to about 250° C., 180 C to 220° C., about 180° C. to about 220° C., 185° C. to 215° C., about 185° C. to about 215° C., about 190° C. to about 210° C., 190° C. to 210° C., 195° C. to 205° C., or about 195° C. to about 205° C. For non-limiting example, organic solvents that meet the criteria of the prior sentence include propane, butane, pentane, and $CO_2$. Combinations of these criteria for preference of certain cannabinoid formulations are contemplated herein.

Other reasons for excluding certain organic solvents from formulations may be unrelated to the rate of cannabinoid uptake, however. For example, an organic solvent may be inappropriate for use with the device materials (corrosive or otherwise incompatible). An organic solvent may be inappropriate for use in inhalation or for toxicity reasons—thus not be compatible for human consumption, ingestion, or inhalation (depending on the embodiment of the composition). An organic solvent that is bitter or otherwise bad-tasting may also provide a reason for exclusion, in some embodiments. Organic solvents that oxidize at room temperature or at operating temperature may be inappropriate for certain embodiments, as this indicates a decomposition or reaction or instability that may be undesirable in the formulation. Decomposition of organic solvents at room or operating temperatures may also indicate that the organic solvent is inappropriate for use in the embodiment formulations. For example, organic solvents that decompose at 175° C., or decomposes at 140° C., for a device operating at 200° C., may not be appropriate. Organic solvents that have poor solubility in the composition constituents may be inappropriate for use in certain embodiments of the compositions herein. For example, cannabinoids with a composition of organic solvents that will not produce a solution at a concentration of 0.5% (w/w) cannabinoid or higher in propylene glycol (PG) or vegetable glycerin (VG) or any mixture of PG and VG at ambient conditions. As used herein, weight percentage (w/w) refers to the weight of the individual component over the weight of the total formulation.

As used in this specification and the claims, the singular forms "a," "an," and "the" include plural referents unless the context clearly dictates otherwise.

The term "organic solvent" as used herein, refers to an organic compound with solvent properties. A non-limiting example of common organic solvents are the alkanes, which are hydrocarbons with no carbon—carbon double or triple bonds.

The term "electronic cigarette" or "e-cigarette" or "aerosol inhalation device" or "low temperature vaporization device" as used herein, refers to an electronic inhaler that vaporizes a liquid solution into an aerosol mist, simulating the act of cannabis smoking. The liquid solution comprises a formulation comprising cannabinoids. There are many electronic cigarettes which do not resemble conventional cigarettes at all. The amount of cannabinoid contained can be chosen by the user via the inhalation. In general, an electronic cigarette contains three essential components: a plastic cartridge that serves as a mouthpiece and a reservoir for liquid, an "atomizer" that vaporizes the liquid, and a battery. Other embodiment electronic cigarettes include a combined atomizer and reservoir, called a "cartomizer" that may or may not be disposable, a mouthpiece that may be integrated with the cartomizer or not, and a battery.

As used in this specification and the claims, unless otherwise stated, the term "about" refers to variations of 1%, 2%, 3%, 4%, 5%, 10%, 15%, 25%, or 50% depending on the embodiment.

Suitable carriers (e.g., a liquid solvent) for the cannabinoids described herein include a medium in which a cannabinoid is soluble at ambient conditions, such that the cannabinoid does not form a solid precipitate. Examples include, but are not limited to, vegetable glycerin, glycerol, propylene glycol, trimethylene glycol, water, ethanol and the like, as well as combinations thereof. In some embodiments, the liquid carrier comprises 0% to 100% of propylene glycol and 100% to 0% of vegetable glycerin. In some embodiments, the liquid carrier comprises 10% to 70% of propylene glycol and 90% to 30% of vegetable glycerin. In some embodiments, the liquid carrier comprises 20% to 50% of propylene glycol and 80% to 50% of vegetable glycerin. In some embodiments, the liquid carrier comprises 30% propylene glycol and 70% vegetable glycerin. In some embodiments, the liquid carrier comprises 50% propylene glycol and 50% vegetable glycerin.

The formulations described herein vary in concentration. In some formulations, a dilute concentration of the cannabinoids in the carrier is utilized. In some formulations, a less dilute concentration of the cannabinoids in the carrier is utilized. In some formulations the concentration of cannabinoids in the cannabinoid formulation is about 1% (w/w) to about 75% (w/w). In some formulations the concentration of cannabinoids in the cannabinoid formulation is about 1% (w/w) to about 50% (w/w). In some formulations the concentration of cannabinoids in the cannabinoid formulation is about 1% (w/w) to about 35% (w/w). In some formulations the concentration of cannabinoids in the cannabinoid formulation is about 1% (w/w) to about 25% (w/w). In some embodiments the concentration of cannabinoids in the cannabinoid formulation is about 1% (w/w) to about 15% (w/w). In some formulations the concentration of cannabinoids in the cannabinoid formulation is about 4% (w/w) to about 12% (w/w). In some formulations the concentration of cannabinoids in the cannabinoid formulation is about 4% (w/w). In some embodiments the concentration of cannabinoids in the cannabinoid formulation is about 2% (w/w). In some formulations the concentration of cannabinoids in the cannabinoid formulation is 1% (w/w) to 25% (w/w). In some formulations the concentration of cannabinoids in the cannabinoid formulation is 1% (w/w) to 20% (w/w). In some formulations the concentration of cannabinoids in the cannabinoid formulation is 1% (w/w) to 18% (w/w). In some formulations the concentration of cannabinoids in the cannabinoid formulation is 1% (w/w) to 15% (w/w). In some formulations the concentration of cannabinoids in the cannabinoid formulation is 4% (w/w) to 12% (w/w). In some formulations the concentration of cannabinoids in the cannabinoid formulation is 4% (w/w). In some formulations the concentration of cannabinoids in the cannabinoid formulation is 2% (w/w). In some formulations, a less dilute concentration of one cannabinoid is used in conjunction with a more dilute concentration of a second cannabinoid. In some formulations, the concentration of cannabinoids in the first cannabinoid formulation is about 1% to about 50%, and is combined with a second cannabinoid formulation having a concentration of cannabinoid therein from about 1% to about 50% or any range or concentration therein. In some formulations, the concentration of cannabinoids in the first cannabinoid formulation is 1% to 25%, and is combined with a second cannabinoid formulation having a concentration of cannabinoids therein from 1% to 25% or any range or concentration therein. As used with respect to concentrations of cannabinoids in the cannabinoid formulations, the term "about" refers to ranges of 0.05% (i.e. if the concentration is about 20%, the range is 19.95%-20.05%), 0.1 (i.e. if the concentration is about 20%, the range is 19.90%-20.10%), 0.25 (i.e. if the concentration is about 20%, the range is 19.75%-20.25%), 0.5 (i.e. if the concentration is about 20%, the range is 19.5%-20.5%), or 1 (i.e. if the concentration is bout 20%, the range is 19%-21%), depending on the embodiment.

In certain embodiments, the cannabinoid is in an amount that forms about 0.5% to about 50% cannabinoid in the inhalable aerosol. In certain embodiments, the cannabinoid is in an amount that forms about 1% to about 50% cannabinoid in the inhalable aerosol. In certain embodiments, the liquid formulation has a cannabinoid concentration of about 1% (w/w) to about 50% (w/w). In certain embodiments s, the liquid formulation has a cannabinoid concentration of about 1% (w/w) to about 45% (w/w). In certain embodiments, the liquid formulation has a cannabinoid concentration of about 1% (w/w) to about 30% (w/w). In certain embodiments, the liquid formulation has a cannabinoid concentration of about 1% (w/w) to about 20% (w/w). In certain embodiments, the liquid formulation has a cannabinoid concentration of about 4% (w/w) to about 15% (w/w). In certain embodiments, the liquid formulation has a cannabinoid concentration of about 10% (w/w). In certain embodiments, the liquid formulation has a cannabinoid concentration of about 5% (w/w).

Cannabinoids are extracted by the introduction of a suitable organic solvent. In some formulations provided herein, suitable organic solvents are alkanes. Examples of alkanes disclosed herein are methane, ethane, propane, butane, pentane, hexane, heptane, octane, nonane, decane, $CO_2$ and the like. In some formulations provided herein, the organic solvents used herein is butane. Cannabinoids are formed from the introduction of an organic solvent to cannabis. In some formulations provided herein, the stoichiometric ratios of the cannabis to organic solvent (cannabis:organic solvent) are 1:10, 1:11, 1:12, 1:13, 2:21, 2:23, 2:25, 3:31, 3:32, 3:34, 3:35, 3:37, 3:38, 4:41, 4:42, 4:43, 4:45, 4:46, 4:47, 4:49, 4:50, 5:51, 5:52, 5:53, 5:54, 5:56, 5:57, 5:58, 5:59, 5:61, 5:62, 5:63, or 5:64. In some formulations provided herein, the stoichiometric ratios of the cannabis to organic solvent are 1:9, 1:8, 1:7, 1:6, or 1:5 (cannabis:organic solvent).

Cannabinoids are a class of diverse chemical compounds that act on cannabinoid receptors in cells that represses neurotransmitter release in the brain. Ligands for these receptor proteins include the endocannabinoids (produced naturally in the body by animals), the phytocannabinoids (found in cannabis and some other plants), and synthetic cannabinoids (manufactured artificially). For non-limiting example the most notable cannabinoid is the phytocannabinoid tetrahydrocannabinol (THC), the primary psychoactive compound in cannabis, and cannabidiol (CBD), another major constituent of the plant. There are at least 125 different cannabinoids isolated from cannabis, exhibiting varied effects. Synthetic cannabinoids encompass a variety of distinct chemical classes: the classical cannabinoids structurally related to THC, the nonclassical cannabinoids (cannabimimetics) including the aminoalkylindoles, 1,5-diarylpyrazoles, quinolines, and arylsulfonamides, as well as eicosanoids related to endocannabinoids.

Cannabinoid formulations may be formed by introducing a suitable organic solvent to cannabis, purging the organic solvent out of the neat mixture at ambient temperature or at elevated temperature, and then diluting the cannabinoid extract with a carrier mixture, such as a mixture of propylene glycol and glycerin. In some embodiments, the suitable organic solvent is completely purged from the cannabinoid extract prior to dilution. The suitable organic solvent may not completely purge from the cannabinoid extract prior to dilution. The addition of the suitable organic solvent to the cannabis to form a neat mixture may cause an endothermic reaction. The addition of the suitable organic solvent to the cannabis to form a neat mixture may be conducted at 15° C. The addition of the suitable organic solvent to the cannabis to form a neat mixture may be conducted at 50° C. The neat mixture may be warmed/cooled to ambient temperature prior to dilution. The dilution may be carried out at elevated temperature.

In certain embodiments, the formulation is non-corrosive to an electronic cigarette. In certain embodiments, the organic solvent is stable at and below operating temperature or about 200° C. In certain embodiments s, the organic solvent does not decompose at and below operating temperature or about 200° C. In certain embodiments, the organic solvent does not oxidize at and below operating temperature or about 200° C. In certain embodiments, the formulation is non-corrosive to the electronic cigarette. In certain embodiments, the formulation is non-toxic to a user of the electronic cigarette.

Cannabinoid formulations may be prepared by combining cannabinoid extract and a suitable organic solvent in a carrier mixture, such as a mixture of propylene glycol and glycerin. The mixture of cannabinoid extract and a first carrier mixture is combined with a mixture of a suitable organic solvent in a second carrier mixture. In some embodiments, the first and second carrier mixtures are identical in composition. In some embodiments, the first and second carrier mixtures are not identical in composition. In some embodiments, heating of cannabinoid/organic solvent/carrier mixture is required to facilitate complete dissolution.

In some embodiments, cannabinoid formulations may be prepared and added to a solution of 3:7 ratio by weight of propylene glycol (PG)/vegetable glycerin (VG), and mixed thoroughly. While described herein as producing 10 g of each of the formulations, all procedures noted infra are scalable. Other manners of formulation may also be employed form the formulations noted infra, without departing from the disclosure herein, and as would be known to one of skill in the art upon reading the disclosure herein.

Figure 3:
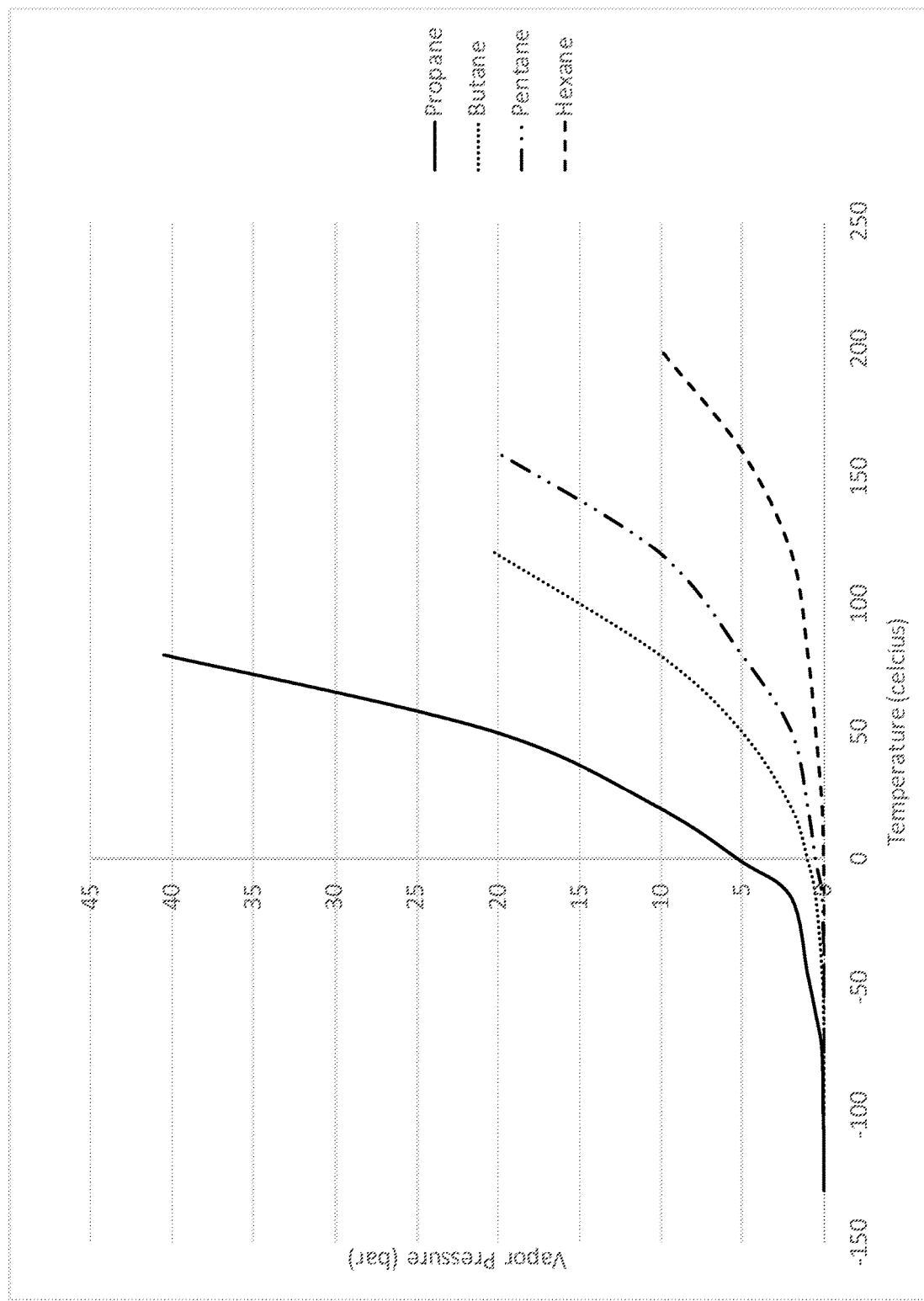
FIG. 3 illustrates the calculated vapor pressures of various organic solvents relative to cannabinoids.

The optimal cannabinoid formulation may be determined by the vapor pressure of the constituent organic solvent. In some embodiments, the cannabinoid formulations comprise an organic solvent with a vapor pressure that is similar to the vapor pressure of other cannabinoid formulations. In some embodiments, the cannabinoid formulations are formed from an organic solvent with a vapor pressure that is similar to the vapor pressure of other cannabinoid formulations at the heating temperature of the device. FIG. 3 illustrates this trend. Cannabinoids formed from cannabis and propane; cannabis and butane; or cannabis and $CO_2$ are concentrated extracts that produce a satisfaction in an individual user consistent with efficient transfer of cannabinoid and a rapid rise in cannabinoid plasma levels. This pattern may be due to the mechanism of action during heating of the cannabinoid formulation. The cannabinoid may disassociate at, or just below, the heating temperature of the device, resulting in a mixture of cannabinoid and the individual organic solvent. At that point, if both the cannabinoid and organic solvent have similar vapor pressures, they may aerosolize at the same time, giving rise to a transfer of both cannabinoid and the constituent organic solvent to the user.

The cannabinoid liquid formulation for generating an inhalable aerosol upon heating in an electronic cigarette may comprise a cannabinoid in a biologically acceptable liquid carrier; wherein the organic solvent used to form said cannabinoids are characterized by a vapor pressure between 100 to 10,000 bar at 25° C. In some embodiments, the organic solvent used to form the cannabinoid is characterized by vapor pressure less than 25 bar at 50° C. In some embodiments, the organic solvent used to form the cannabinoid is characterized by vapor pressure between 10-10,000 bar at 25° C.

Different cannabinoid formulations produced varying degrees of satisfaction in an individual. In some embodiments, the concentration of the cannabinoid affected satisfaction, such that increased concentration was more satisfying as compared to less concentration. The cannabinoid formed may be highly concentrated. The cannabinoid formed may be less concentrated. The cannabinoid may exist in more than one concentration state, e.g., an equilibrium of low and highly concentrated cannabinoids. The extent of concentration of the cannabinoid molecule may be dependent upon the stoichiometric ratio of cannabis:organic solvent used in the cannabinoid formation reaction. The extent of concentration of the cannabinoid molecule may be dependent upon the solvent. The extent of concentration of the cannabinoid molecule may be unknown. In some embodiments, highly concentrated cannabinoid formulations produced a high degree of satisfaction in the user. The reason for this trend may be explained by a mechanism of action wherein the cannabinoid is first separated prior to transfer to the vapor with the constituent acceptable liquid carrier and then retained and stabilized after by the organic solvent going down stream to the lungs of the user. It may be possible to modify the acceptable liquid carrier, thus resulting in better transfer efficiency. In addition, the lack of satisfaction of some cannabinoids indicates that a second factor may be important. A cannabinoid may be best performing when it is at its optimal extent vaporization, depending on the formulation. For example, cannabinoids with a cannabinoid ratio of 1:2 (cannabinoid:acceptable liquid carrier), may deliver less satisfaction to the user than the one containing same amount of cannabinoids but only half amount of acceptable liquid carrier, i.e. cannabinoid: acceptable liquid carrier (1:1). This may be explained as 1 mole of cannabinoids produces a formulation with 2 moles of acceptable liquid carrier. When there is not enough cannabinoid to associate with all the acceptable liquid carrier molecules, the cannabinoids left in the formulation may reduce the satisfaction, pain relief, and therapeutic benefits the formulation provides.

The flavor of the constituent organic solvent used in the extract formation may be a consideration in choosing the organic solvent. A suitable organic solvent may have minimal or no toxicity to humans in the concentrations used. A suitable organic solvent may be compatible with the electronic cigarette components it contacts or could contact at the concentrations used. That is, such organic solvent does not degrade or otherwise react with the electronic cigarette components it contacts or could contact. The odor of the constituent organic solvent used in the extract formation may be a consideration in choosing a suitable organic solvent. The concentration of the cannabinoid in the carrier may affect the satisfaction in the individual user. In some embodiments, the flavor of the formulation is adjusted by changing the organic solvent. In some embodiments, the flavor of the formulation is adjusted by adding exogenous flavorants. In some embodiments, an unpleasant tasting or smelling organic solvent is used in minimal quantities to mitigate such characteristics. In some embodiments, exogenous pleasant smelling or tasting organic solvent is added to the formulation.

Cannabinoid formulations may generate an inhalable aerosol upon heating in an electronic cigarette. The amount of cannabinoid or cannabinoid aerosol inhaled may be user-determined. The user may, for example, modify the amount of cannabinoid or cannabinoids inhaled by adjusting inhalation strength.

Formulations are described herein comprising two or more cannabinoids. In some embodiments, wherein a formulation comprises two or more cannabinoids, each individual cannabinoid is formed as described herein.

Cannabinoid formulations, as used herein, refer to a single or mixture of cannabinoids with other suitable chemical components used for e-cigarette, such as carriers, stabilizers, diluents, dispersing agents, suspending agents, thickening agents, and/or excipients. In certain embodiments, the cannabinoid formulation is stirred at ambient conditions for 20 minutes. In certain embodiments, the cannabinoid formulation is heated and stirred at 55 C for 20 minutes. In certain embodiments, the cannabinoid formulation is heated and stirred at 90 C for 60 minutes. In certain embodiments, the formulation facilitates administration of cannabinoid to an organism (e.g., lung).

The cannabinoids of cannabinoid formulations provided herein are either naturally occurring cannabinoids (e.g., from extract of cannabinoid containing species such as cannabis), or synthetic cannabinoids. In some embodiments, the cannabinoid is employed in relatively pure form (e.g., greater than about 80% pure, 85% pure, 90% pure, 95% pure, or 99% pure). In some embodiments, the cannabinoid for cannabinoid formulation provided herein is "water clear" in appearance in order to avoid or minimize the formation of tarry residues during the subsequent extract formation steps.

Cannabinoid formulations used for e-cigarettes described herein, in some embodiments, have a cannabinoid concentration of about 0.5% (w/w) to about 80% (w/w), wherein the concentration is of cannabinoid weight to total solution weight, i.e. (w/w). In certain embodiments, cannabinoid formulations provided herein have a cannabinoid concentration of about 1% (w/w) to about 80% (w/w). In certain embodiments, cannabinoid formulations provided herein have a cannabinoid concentration of about 1% (w/w) to about 50% (w/w). In certain embodiments, cannabinoid formulations provided herein have a cannabinoid concentration of about 1% (w/w) to about 35% (w/w). In certain embodiments, cannabinoid formulations provided herein have a cannabinoid concentration of about 4% (w/w) to about 25% (w/w). In certain embodiments, cannabinoid formulations provided herein have a cannabinoid concentration of about 1% (w/w) to about 35% (w/w), about 3% (w/w) to about 25% (w/w), or about 4% (w/w) to about 15% (w/w). In certain embodiments, cannabinoid formulations provided herein have a cannabinoid concentration of about 0.5% (w/w) to about 10% (w/w). In certain embodiments, cannabinoid formulations provided herein have a cannabinoid concentration of about 0.5% (w/w) to about 5% (w/w). In certain embodiments, cannabinoid formulations provided herein have a cannabinoid concentration of about 0.5% (w/w) to about 4% (w/w). In certain embodiments, cannabinoid formulations provided herein have a cannabinoid concentration of about 0.5% (w/w) to about 3% (w/w). In certain embodiments, cannabinoid formulations provided herein have a cannabinoid concentration of about 0.5% (w/w) to about 2% (w/w). In certain embodiments, cannabinoid formulations provided herein have a cannabinoid concentration of about 0.5% (w/w) to about 1% (w/w). In certain embodiments, cannabinoid formulations provided herein have a cannabinoid concentration of about 1% (w/w) to about 10% (w/w). In certain embodiments, cannabinoid formulations provided herein have a cannabinoid concentration of about 1% (w/w) to about 5% (w/w). In certain embodiments, cannabinoid formulations provided herein have a cannabinoid concentration of about 1% (w/w) to about 4% (w/w). In certain embodiments, cannabinoid formulations provided herein have a cannabinoid concentration of about 1% (w/w) to about 3% (w/w). In certain embodiments, cannabinoid formulations provided herein have a cannabinoid concentration of about 1% (w/w) to about 2% (w/w). In certain embodiments, cannabinoid formulations provided herein have a cannabinoid concentration of about 2% (w/w) to about 10% (w/w). In certain embodiments, cannabinoid formulations provided herein have a cannabinoid concentration of about 2% (w/w) to about 5% (w/w). In certain embodiments, cannabinoid formulations provided herein have a cannabinoid concentration of about 2% (w/w) to about 4% (w/w). Certain embodiments provide a cannabinoid formulation having a cannabinoid concentration of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, 20%, 25%, 30%, 35%, 40%, 45%, 50%, 60%, 70%, 80%, or 90% (w/w), or more, including any increments therein. Certain embodiments provide a cannabinoid formulation having a cannabinoid concentration of about 50% (w/w). Certain embodiments provide a cannabinoid formulation having a cannabinoid concentration of about 40% (w/w). Certain embodiments provide a cannabinoid formulation having a cannabinoid concentration of about 30% (w/w). Certain embodiments provide a cannabinoid formulation having a cannabinoid concentration of about 20% (w/w). Certain embodiments provide a cannabinoid formulation having a cannabinoid concentration of about 10% (w/w). Certain embodiments provide a cannabinoid formulation having a cannabinoid concentration of about 5% (w/w).

The formulation further may comprise one or more flavorants.

The suitable organic solvent for the cannabinoid formulation may have a vapor pressure <25 bar at 50° C. and is non-corrosive to the electronic cigarette or is non-toxic to humans. In some embodiments, the suitable organic solvent for cannabinoid formation is selected from the aforementioned group.

The suitable organic solvent for the cannabinoid formulation may have a vapor pressure of about 100 to 10,000 bar at 25° C. and is non-corrosive to the electronic cigarette or is non-toxic to humans. In some embodiments, the suitable organic solvent for cannabinoid formation is selected from the aforementioned group.

The suitable organic solvent for the cannabinoid formulation may have a melting point <55° C., a boiling point >–165° C., at least a 15-degree difference between the melting point and the boiling point, and is non-corrosive to the electronic cigarette or is non-toxic to humans. In some embodiments, the suitable organic solvent for cannabinoid formation has a melting point at least 20 degrees lower than the operating temperature of the electronic cigarette, a boiling point no more than 300 degrees lower than the operating temperature of the electronic cigarette, at least a 15-degree difference between the melting point and the boiling point, and is non-corrosive to the electronic cigarette or is non-toxic to humans; wherein the operating temperature is 200° C. In some embodiments, the suitable organic solvent for cannabinoid formation is selected from the aforementioned group.

The suitable organic solvent for the cannabinoid formulation does not decompose at the operating temperature of the electronic cigarette. In some embodiments, the suitable organic solvent for cannabinoid formation does not oxidize at the operating temperature of the electronic cigarette. In some embodiments, the suitable organic solvent for cannabinoid formation does not oxidize at room temperature. In some embodiments, the suitable organic solvent for cannabinoid formation does not provide an unpleasant taste. In some embodiments, the suitable organic solvent for cannabinoid formation has good solubility in a liquid formulation for use in an electronic cigarette.

Figure 7:
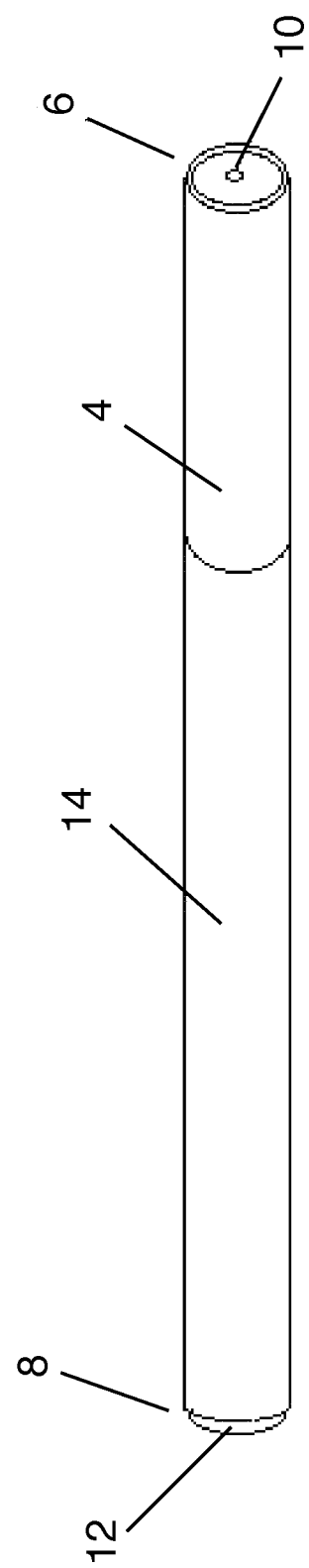
FIG. 7 depicts an example embodiment of an electronic cigarette having a fluid storage compartment comprising an embodiment cannabinoid formulation described herein.

Provided herein is an electronic cigarette 2 having a fluid storage compartment 4 comprising an embodiment cannabinoid formulation of any embodiment described herein within the fluid storage compartment described herein. An embodiment is shown in FIG. 7. The electronic cigarette 2 of FIG. 7 includes a mouth end 6, and a charging end 8. The mouth-end 6 includes a mouthpiece 10. The charging end 8 may connect to a battery or a charger or both, wherein the battery is within a body of the electronic cigarette, and the charger is separate from the battery and couples to the body or the battery to charge the battery. In some embodiments the electronic cigarette comprises a rechargeable battery within a body 14 of the electronic cigarette and the charge end 8 comprises a connection 12 for charging the rechargeable battery. In some embodiments, the electronic cigarette comprises a cartomizer that comprises the fluid storage compartment and an atomizer. In some embodiments, the atomizer comprises a heater. In some embodiments the fluid storage compartment 4 is separable from an atomizer. In some embodiments the fluid storage compartment 4 is replaceable as part of a replaceable cartridge. In some embodiments the fluid storage compartment 4 is refillable. In some embodiments, the mouthpiece 10 is replaceable.

Figure 8:
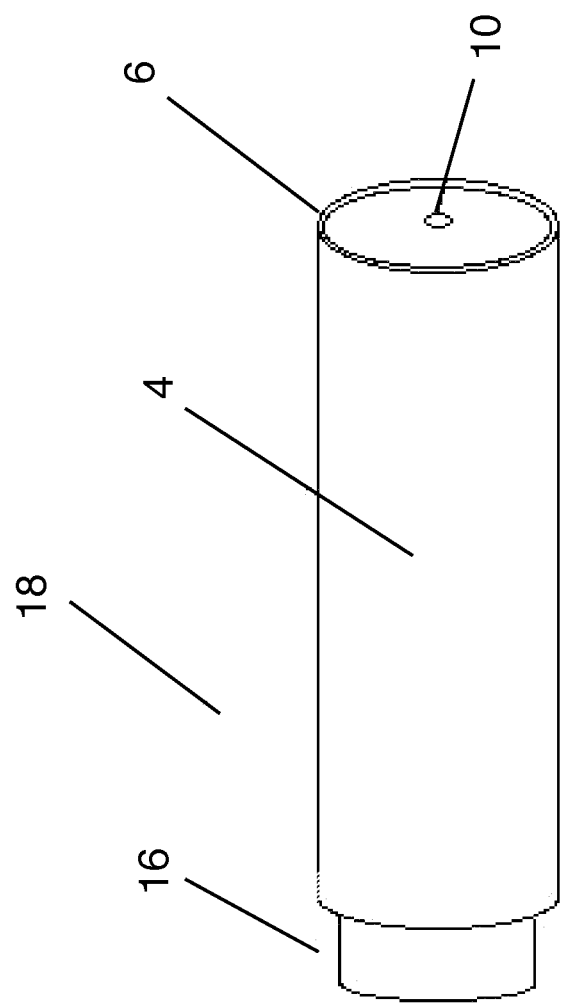
FIG. 8 depicts an example embodiment of an electronic cigarette cartomizer having a fluid storage compartment, a heater, and comprising an embodiment cannabinoid formulation described herein.

Provided herein is a cartomizer 18 for an electronic cigarette 2 having a fluid storage compartment 4 comprising an embodiment cannabinoid formulation of any embodiment described herein within the fluid storage compartment described herein. The cartomizer 18 embodiment of FIG. 8 includes a mouth end 6, and a connection end 16. The connection end 16 in the embodiment of FIG. 8 couples the cartomizer 14 to a body of an electronic cigarette, or to a battery of the electronic cigarette, or both. The mouth end 6 includes a mouthpiece 10. In some embodiments, the cartomizer does not include a mouthpiece, and in such embodiments, the cartomizer can be coupled to a mouthpiece of an electronic cigarette, or the cartomizer can be coupled to a battery or body of an electronic cigarette, while the mouthpiece is also coupled to the battery or the body of the electronic cigarette. In some embodiments, the mouthpiece is integral with the body of the electronic cigarette. In some embodiments, including the embodiment of FIG. 8, the cartomizer 18 comprises the fluid storage compartment 4 and an atomizer (not shown). In some embodiments, the atomizer comprises a heater (not shown).

EXAMPLES

The Examples that follow are illustrative of specific embodiments disclosed herein and various uses thereof. They are set forth for explanatory purposes only and are not to be taken as limiting.

Example 1

Preparation of Cannabinoid Formulations

Various cannabinoid formulations were prepared and added to a liquid carrier solution of 8:2 ratio by weight of propylene glycol (PG)/vegetable glycerin (VG), and mixed thoroughly. The examples shown below were used to make 10 g of each of the formulations. All procedures are scalable.

For example, in order to make cannabinoid formulations with a final cannabinoid equivalent concentration of 30% (w/w), the following procedures were applied to each individual formulation.

Cannabinoid formulation: 8 ml liquid carrier was added to a beaker followed by adding 4 g cannabinoid extract to the same beaker. The mixture was stirred at 55° C. for 20 minutes until the cannabinoid extract was completely dissolved and an orange oily mixture was formed. The mixture was cooled down to ambient conditions, and the mixture was stirred until a visually homogenous formulation solution was achieved.

Cannabinoid formulation can also be made by adding 4 mL liquid carrier to a beaker followed by adding 4 g cannabinoid extract and 4 mL PGN G (8:2) solution to the same beaker. The mixture was then stirred at 55° C. for 20 minutes until a visually homogenous formulation solution was achieved with no undissolved cannabinoid extract. Cannabinoid formulation was made by adding 8 mL liquid carrier to a beaker followed by adding 4 g cannabinoid extract and 8 mL PGN G (8:2) solution to the same beaker. The mixture was then stirred at 90° C. for 60 minutes until a visually homogenous formulation solution was achieved with no undissolved chemicals.

Cannabinoid formulation was made by adding 4 mL liquid carrier to a beaker followed by adding 4 g cannabinoid extract and 4 mL PGN G (8:2) solution to the same beaker. The mixture was then stirred at 90° C. for 60 minutes until a visually homogenous formulation solution was achieved with no undissolved chemicals.

Cannabinoid formulation can also be made by adding 4 mL liquid carrier to a beaker followed by adding 4 g cannabinoid extract to the same beaker. The mixture was stirred at 90° C. for 60 minutes until completely dissolved and an orange oily mixture was formed. The mixture was either cooled to ambient conditions or kept at 90° C. when 4 mL PGN G (8:2) solution was added. The mixture was then stirred at 90° C. until a visually homogenous formulation solution was achieved with no undissolved chemicals.

Cannabinoid formulation was made by adding 4 g cannabinoid to a beaker followed by adding 8 mL PGN G (8:2) solution to the same beaker. The mixture was then stirred at ambient conditions for 10 minutes until a visually homogenous formulation solution was achieved.

For example, in order to make cannabinoid formulations with a final cannabinoid equivalent concentration of 45% (w/w), the following procedures were applied to each individual formulation.

Cannabinoid formulation: 6 mL liquid carrier was added to a beaker followed by adding 6 g cannabinoid extract to the same beaker. The mixture was stirred at 55° C. for 20 minutes until completely dissolved and an orange oily mixture was formed. The mixture was cooled down to ambient conditions. and the blend was stirred until a visually homogenous formulation solution was achieved.

Cannabinoid formulation can also be made by adding 4 mL liquid carrier to a beaker followed by adding 6 g cannabinoid extract and 2 mL PGN G (8:2) solution to the same beaker. The mixture was then stirred at 55° C. for 20 minutes until a visually homogenous formulation solution was achieved with no undissolved chemicals.

Cannabinoid formulation was made by adding 6 mL PG to a beaker followed by adding 6 g cannabinoid extract to the same beaker. The mixture was then stirred at 90° C. for 60 minutes until a visually homogenous formulation solution was achieved with no undissolved chemicals.

Cannabinoid formulation was made by adding 4 mL liquid carrier to a beaker followed by adding 6 g cannabinoid extract and 2 mL PGN G (8:2) solution to the same beaker. The mixture was then stirred at 90° C. for 60 minutes until a visually homogenous formulation solution was achieved with no undissolved chemicals.

Cannabinoid formulation was made by adding melted 6 g cannabinoid extract to a beaker followed by adding 4 mL liquid carrier to the same beaker. The mixture was stirred at ambient conditions for 10 minutes, and an oily product was produced. The mixture was allowed to cool down to ambient temperature and 2 mL PGN G (8:2) solution was added to the same beaker. The mixture was then stirred at ambient conditions for 20 minutes until a visually homogenous formulation solution was achieved.

Cannabinoid formulation was made by adding 6 mL liquid carrier to a beaker followed by adding 6 g cannabinoid extract to the same beaker. The mixture was stirred at ambient conditions for 10 minutes, and oily product was produced. The mixture was allowed to remain at ambient temperature then the mixture was then stirred at ambient conditions for 20 minutes until a visually homogenous formulation solution was achieved.

For example, in order to make cannabinoid formulations with a final cannabinoid equivalent concentration of 15% (w/w), the following procedures were applied to each individual formulation.

Cannabinoid formulation: 4 mL liquid carrier was added to a beaker followed by adding 2 g cannabinoid extract to the same beaker. The mixture was stirred at 55° C. for 20 minutes until completely dissolved and an orange oily mixture was formed. The mixture was cooled down to ambient conditions. 6 mL PGN G (8:2) solution was added to the orange cannabinoid mixture and the blend was stirred until a visually homogenous formulation solution was achieved.

Cannabinoid formulation can also be made by adding 10 mL carrier liquid to a beaker followed by adding 2 g cannabinoid extract to the same beaker. The mixture was then stirred at 55° C. for 20 minutes until a visually homogenous formulation solution was achieved with no undissolved chemicals.

For example, in order to make cannabinoid formulations with a final cannabinoid equivalent concentration of 3.75% (w/w), the following procedures were applied to each individual formulation.

Cannabinoid formulation: 1.5 mL liquid carrier was added to a beaker followed by adding 0.5 g cannabinoid extract to the same beaker. The mixture was stirred at 55° C. for 20 minutes until completely dissolved and an orange oily mixture was formed. The mixture was cooled down to ambient conditions. 10 mL PGN G (8:2) solution was added to the orange cannabinoid mixture and the blend was stirred until a visually homogenous formulation solution was achieved.

Cannabinoid formulation can also be made by adding 11.5 mL liquid carrier to a beaker followed by adding 0.5 g cannabinoid extract to the same beaker. The mixture was then stirred at 55° C. for 20 minutes until a visually homogenous formulation solution was achieved with no undissolved chemicals.

Cannabinoid formulation was made by adding 11.5 mL liquid carrier to a beaker followed by adding 0.5 g cannabinoid extract to the same beaker. The mixture was then stirred at 90° C. for 60 minutes until a visually homogenous formulation solution was achieved with no undissolved cannabinoid extract.

Cannabinoid formulation was made by adding melted 0.5 g cannabinoid extract to a beaker followed by adding 11.5 mL liquid carrier to the same beaker. The mixture was stirred at ambient conditions for 10 minutes, and an oily product was produced. The mixture was allowed to remain at ambient temperature and the mixture was then stirred at ambient conditions for 20 minutes until a visually homogenous formulation solution was achieved.

Cannabinoid formulation was made by adding 1.5 mL liquid carrier to a beaker followed by adding 0.5 g cannabinoid extract to the same beaker. The mixture was stirred at ambient conditions for 10 minutes, and an oily product was produced. The mixture was allowed to cool down to ambient temperature and 10 mL PGN G (8:2) solution was added to the same beaker. The mixture was then stirred at ambient conditions for 20 minutes until a visually homogenous formulation solution was achieved.

Various formulations comprising different cannabinoids can be prepared similarly, or different concentrations of the above-noted cannabinoid formulations or other cannabinoid formulations or other liquid carrier ratios of PG:VG can be prepared as one of skill in the art would know to do upon reading the disclosure herein.

Various formulations comprising two or more cannabinoids can be prepared similarly in a solution of 8:2 ratio of propylene glycol (PG)/vegetable glycerin (VG). For example, 1 g (90% w/w cannabinoid) of cannabinoid CBD and 1 g (90% w/w cannabinoid) of cannabinoid THC are added to 10 mL of PGN G solution, to achieve a 15% w/w cannabinoid formulation.

Also provided is another exemplary formulation. For example, 0.67 g (90% w/w cannabinoid) of cannabinoid CBD, 0.67 g (90% w/w cannabinoid) of cannabinoid THC and 0.67 g (90% w/w cannabinoid) of cannabinoid CBN are added to 9 mL of PGN G solution, to achieve a 15% w/w cannabinoid formulation.

Example 2

Heart Rate Study of Cannabinoid Solutions

Exemplary formulations of cannabinoids, and a control of placebo were prepared and administered in similar fashion to an electronic cigarette to the human subjects. The formulations were designated as low dose (1.8%) cannabinoid, and high-dose (3.9%) cannabinoid.

Baseline heart rate measurements were conducted immediately prior to the consumption of cannabinoids. Measurements were continuously taken at predetermined intervals up to 200 minutes. Final results were presented in FIG. 1.

FIG. 1 summarizes results from heart rate measurements taken for cannabinoid formulations. For ease of reference in reviewing FIG. 1, at the 60-minute time-point, from top to bottom (highest heart rate to lowest heart rate), the cannabinoid formulations are as follows: high-dose cannabinoid, low-dose cannabinoid, and placebo. The test formulations comprising a cannabinoid cause a faster and more significant rise in heart rate than the placebo. The test formulations comprising a high dose cannabinoid also cause faster and more significant rise when compared with a low dose cannabinoid formulation with the same amount of cannabinoid by weight. In turn, the cannabinoids (e.g., CBD, or THC) prepared from the organic solvents having calculated vapor pressures between 100 to 10,000 bar at 25° C., or <25 bar @50° C. cause a faster rise in heart rate than placebo. The cannabinoids prepared from the organic solvents also cause a more significant heart rate increase than placebo. Thus, other suitable cannabinoids formed by the organic solvents with the similar vapor pressure and/or similar boiling point may be used in accordance with the practice of the present invention.

Example 3

Satisfaction Study of Cannabinoid Solution Via E-Cigarette

In addition to the heart rate study shown in Example 2, cannabinoid formulations were used to conduct a satisfaction study in 10 test participants. The test participant, an e-cigarette and/or traditional cigarette user, was required to have no cannabinoid intake for at least 24 hours before the test. The participants took 3 puffs using an e-cigarette or electronic vaporization device over 5 minutes in each case, and then was asked to rate the level of physical and emotional satisfaction he or she felt on a scale of 0-5, with 0 being no physical or emotional satisfaction. The results indicated that all cannabinoid formulations performed well and/or better than a traditional cannabis cigarette.

Based on the Satisfaction Study, the cannabinoids formulations formed with organic solvents having vapor pressure ranges between 100 to 10,000 bar @25° C., or <25 bar @50° C. provide more satisfaction than oral or a traditional cannabis cigarette.

Example 4

Test Formulation 1 (TF1)

A solution of cannabinoids in propylene glycol comprising: 1 g (90% w/w) of cannabinoid extract and 2 mL of propylene glycol—Total volume 3 mL.

Cannabinoid extract was added to the propylene glycol, and mixed thoroughly. In a 1:2 molar ratio the percentage of cannabinoids in the cannabinoid formulation by weight is given by: (1 g/3 mL)90=30% (w/w).

Example 5

Test formulation 2 (TF2)

A solution of cannabinoid in propylene glycol comprising 1 g (90% w/w) of cannabinoid extract was dissolved in 1 mL of propylene glycol and mixed thoroughly.

Example 6

Heart Rate Study of Cannabinoid Solutions Via E-Cigarette

Representative formulations (TF1 and TF2) were administered in similar fashion to an electronic cigarette to human subjects. The operating temperature of the e-cigarette is from about 75° C. to about 325° C., or from about 100° C. to about 300° C.

The atomizer coils in both cases had a resistance of either: 0.9 ohms, and the electronic vaporization device was set to 5V, resulting in 27.8 W of power; or 0.2 ohms, and the electronic vaporization device was set to the "variable wattage" setting thus allowing the atomizer coils no maintain a consistent temperature (250° C.) throughout vaporization (P=V^2/R)

Heart rate was measured in a 30-second interval for 200 minutes from start of puffing. Test participants took puffs ad libitum over 5 minutes in each case (solid line (highest peak): cannabis cigarette, dark dotted line ($3^{rd}$ highest peak): test formulation 1 (TF1—low-dose cannabinoid formulation), light dashed line ($2^{nd}$ highest peak): test formulation 2 (TF2—high-dose cannabinoid formulation). Comparison between cannabis cigarette, TF1, and TF2 is shown in FIG. 2.

Figure 2:
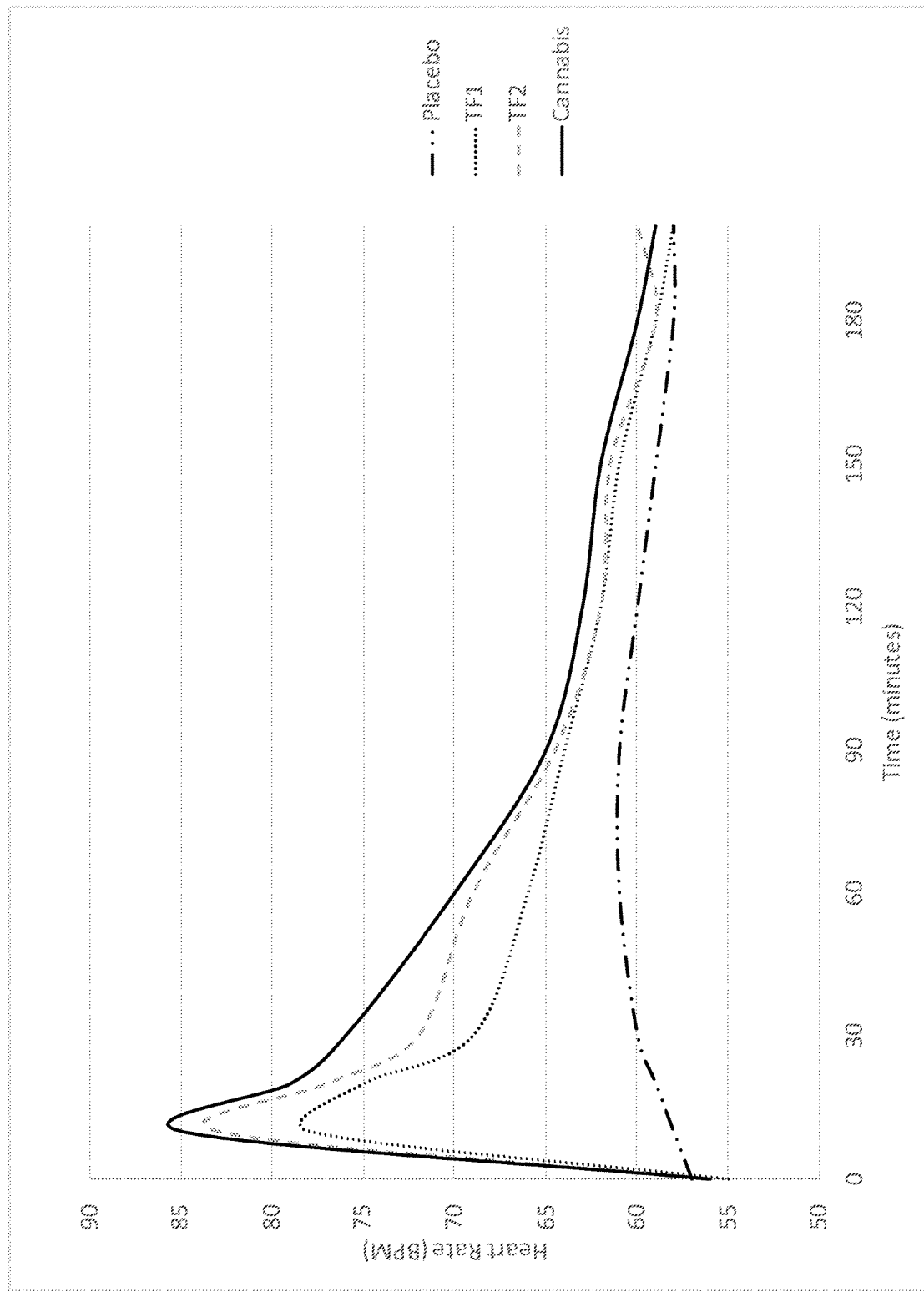
FIG. 2 illustrates results of heart rate data measured for 200 minutes from start of puffing. Y-axis is heart rate (bpm) and X-axis represents duration of the test (0 to 200 minutes)

It is clearly shown in FIG. 2 that the test formulation with high-dose cannabinoid (TF2) causes a faster rise in heart rate than low-dose cannabinoid (TF1). Also, TF2 more closely resembles the rate of increase for a cannabis cigarette. Thus, other suitable cannabinoids that cause the similar effect may be used in accordance with the practice of the present invention. This experience of increased heart rate comparable to that of a traditional burned cannabis cigarette has not been demonstrated or identified in other electronic cigarette devices, nor has it been demonstrated or identified in low temperature cannabis vaporization devices that do not burn the cannabis.

In addition, the data appears to correlate well with the previous findings shown in FIG. 2.

As previously noted in the Satisfaction Study, the cannabinoid formulations with organic solvents having vapor pressures between 100 to 10,000 bar @25° C. and/or <25 bar @50° C. provide more satisfaction than the rest, as noted in FIG. 3. Based on the findings herein, it was anticipated that these cannabinoid formulations having either:

a Vapor Pressure between 100-10,000 bar @25° C., a Vapor Pressure >25 bar@50° C., a difference between boiling point and melting point of at least 15° C., and a boiling point greater than −165° C., and a melting point less than 55° C., a difference between boiling point and melting point of at least 15° C., and a boiling point greater than −165° C., and a melting point less than 55° C., a difference between boiling point and melting point of at least 15° C., and a boiling point at most 300° C. less than operating temperature, and a melting point at least 20° C. lower than operating temperature, or a combination thereof produce one or more of the following effects:

$T_{max}$—Time to maximum blood concentration: Based on the results established herein, a user of an e-cigarette comprising the cannabinoid formulation will experience a comparable rate of physical and emotional satisfaction from using a formulation comprising a mixture of cannabinoids prepared with an appropriate organic solvent at least 1.2× to 3× faster than baseline. As illustrated in FIG. 1: cannabinoids from a low-dose cannabinoid formulation appears to generate a heartbeat that is nearly 1.2 times that of a normal heart rate for an individual approximately 10 minutes after the commencement of puffing; whereas the cannabinoid from a high-dose cannabinoid formulation appears to generate a heartbeat that is nearly 1.3 times that of a normal heart rate for an individual approximately 10 minutes after the commencement of puffing.

Again this would not be inconsistent with the data from FIG. 2, where the data illustrated that at approximately 10 minutes, the heart rate of test participants reached a maximum of 84-87 bpm with either a traditional cannabis cigarette or a cannabinoid formulation (TF2); whereas those same participants heart rates only reached a maximum of approximately 78 bpm at approximately 10 minutes with a cannabinoid formulation (TF1); also a difference in effect of 1.2 times greater with administration of cannabinoid formulations (and traditional cannabis cigarettes) versus placebo (normal heart rate).

Further, when considering peak satisfaction levels (achieved at approximately 10 minutes from the initiation of puffing (time=0) and looking at the slope of the line for plasma concentrations, the approximate slope of those cannabinoid formulations that exceeded oral cannabinoid formulations range between 3.1307 hrn/sec and 2.3442 hrn/sec. By comparison, the average slope of the line for the oral cannabinoid formulations is about 0.418. This would suggest that the concentration of available cannabinoid will be delivered to the user at a rate that is between 5.6 and 7.5 times faster than an oral formulation.

In another measure of performance; $C_{max}$—Maximum blood cannabinoid concentration; it is anticipated that similar rates of increase will be measured in blood cannabinoid concentration, as those illustrated above. That is, it was anticipated based on the findings herein, and unexpected based on the art known to date, that there would be comparable $C_{max}$ between the common cannabis cigarette and certain cannabinoid formulations, but with a lower $C_{max}$ in a cannabinoid solution.

Similarly, anticipated based on the findings herein, certain cannabinoid formulations would have higher rate of cannabinoid uptake levels in the blood at early time periods. Indeed, Example 8 presents data for multiple cannabinoid formulations consistent with these predictions which were made based on the findings and tests noted herein.

Example 7

Heart Rate Study of Cannabinoid Solutions Via E-Cigarette

Exemplary formulations of cannabinoids and a control of propylene glycol are prepared as noted in Example 1 and are administered in the same fashion by an electronic cigarette to the same human subject. About 3 mL of each solution is loaded into an electronic vaporization device's atomizer to be used in the study. The atomizer is then attached to an electronic vaporization device (same manufacturer). The operating temperature of the e-cigarette is from about 75° C. to about 325° C., or from about 100° C. to about 300° C.

Heart rate measurements are taken for 200 minutes; from 10 minutes before start of puffing, for 10 minutes during puffing, and continuing until 190 minutes after end of puffing. The test participant takes puffs ad libitum over 5 minutes in each case. The base heart rate is the average heart rate over the first 10 minutes before start of puffing. Heart rate after puffing started is averaged over 1 minute intervals.

Example 8

Blood Plasma Testing

Blood plasma testing was conducted on eleven subjects (n=11). Seven test articles were used in this study: one reference cannabis cigarette and six blends either administered orally, or used in a electronic vaporizing device having an operating temperature of the e-cigarette from about 75° C. to about 325° C., or from about 100° C. to about 300° C. The reference cannabis cigarette was obtained from the U.S. National Institute on Drug Abuse NIDA). The blends were formulations prepared as described in Example 1.

The concentration of cannabinoid in each of the formulations was confirmed using spectroscopic analysis including UV absorbance, infrared-spectral analysis, (GC-) mass spectrometry, and spectrophotometric analysis. Cannabinoids that were available as calibrated certified standards were diluted to a concentration of 0.01 mg/mL in ethanol to determine analyze molar extinction coefficients in the range of 200 to 400 nm. The control/bank measurement was obtained with ethanol. UV-spectra were recorded using a Varian Cary 1 Bio UV-Visible spectrophotometer controlled by Cary 1/3E system software, version 3.02. A sample cell of 10 mm was used for all measurements. Cannabinoid concentrations reported for all formulations were within the range of 95%-105% of the claimed concentrations All subjects were able to consume about 40 mg of cannabinoid in each tested blend.

Blood and plasma cannabinoid concentration results:
Low-dose formulation: $T_{max}$=0.17 h (0.15-0.25), $C_{max}$=48.6 µg/L (2.3-102)
High-dose formulation: $T_{max}$=0.17 h (0.12-0.37), $C_{max}$=97.8 µg/L (24.5-339)

Figure 4:
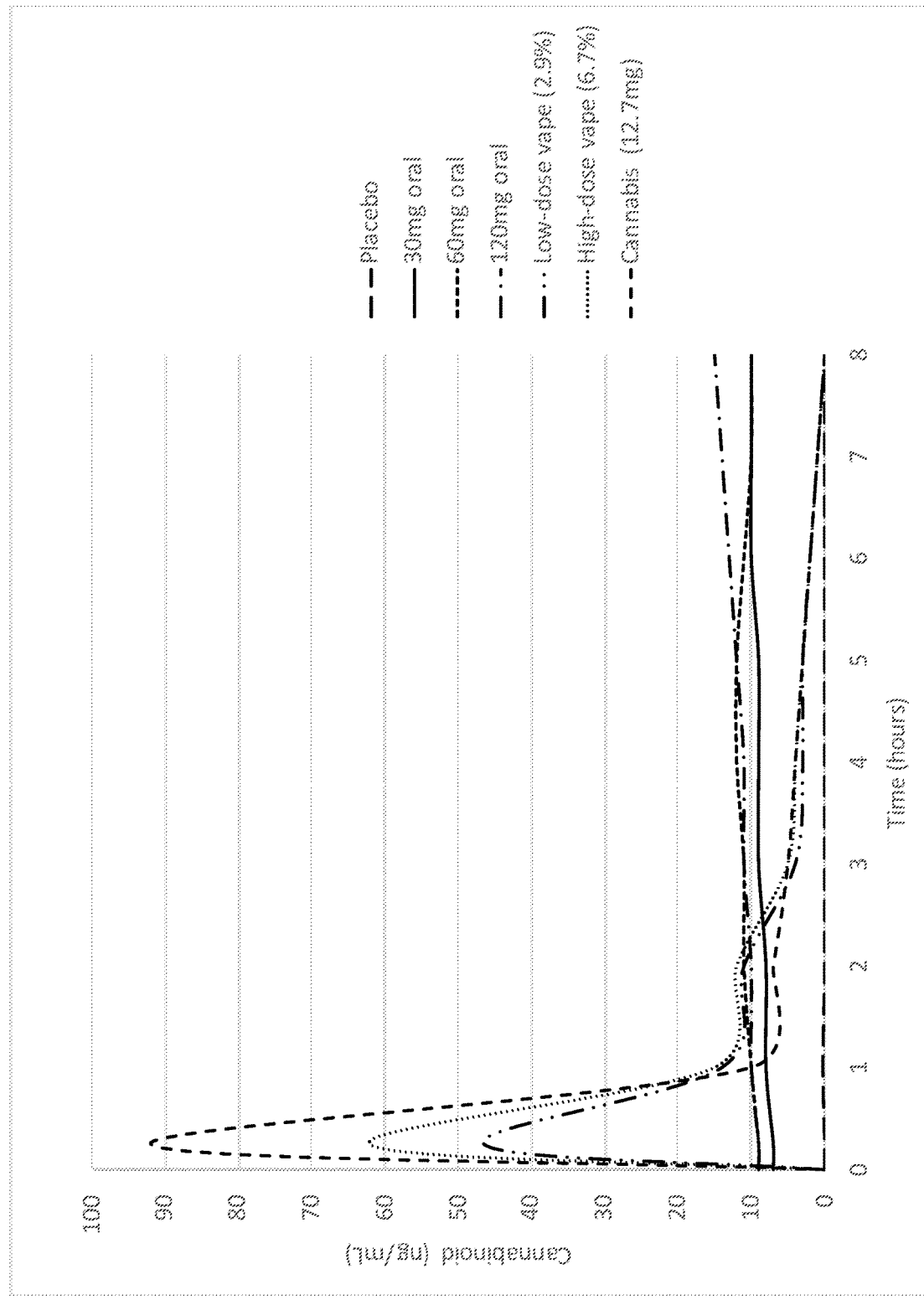
FIG. 4 illustrates the pharmacokinetic profiles for seven test articles in a blood plasma study.

Estimated $C_{max}$ of 30% cannabinoid blends:
$C_{max}$=Mass consumed*Strength*Bioavailability I (Vol of Distribution*Body Weight)=40 mg*30%*30% I (3.4 L/kg*75 kg)=14.12 ng/mL
Estimated $C_{max}$ of 45% cannabinoid blends:
$C_{max}$=Mass consumed*Strength*Bioavailability I (Vol of Distribution*Body Weight)=40 mg*45%*30% I (3.4 L/kg*75 kg)=21.18 ng/mL Pharmacokinetic profiles of the blood plasma testing are shown in FIG. 4;

showing blood cannabinoid concentrations (m/L) over time after oral administration, the first puff (inhalation) of the vaporized aerosol, or the smoke of the cannabis cigarette. Puffs were taken ad libitum starting at time=0 and continuing for 10 minutes. For ease of reference and review of FIG. 4, at the 25-minute time-point, the curves on the graph show from top to bottom (highest average blood cannabinoid concentration to lowest average blood cannabinoid concentration) are cannabis cigarette, high-dose cannabinoid, low-dose cannabinoid, 120 mg oral, 60 mg oral, 30 mg oral, and placebo. Although noted as highest to lowest at this time point, this is not to say that there is a statistically significant difference between any of the cannabinoid formulations, or between any of the cannabinoid formulations and the cannabis cigarette. However, it is possible there may be a statistically significant difference between the $C_{max}$ of particular cannabinoid formulations, and it is also likely based on the data shown in FIG. 4 and in other studies herein that the oral cannabinoid formulation is statistically different from cannabinoid formulations and/or the cannabis cigarette with respect to $C_{max}$, since it appears lower than others tested at several time points. One of skill in the art, upon review of the disclosure herein could properly power a test to determine actual statistically based differences between one or more formulations and the cigarette, or between the formulations themselves in an e-cigarette.

Figure 5:
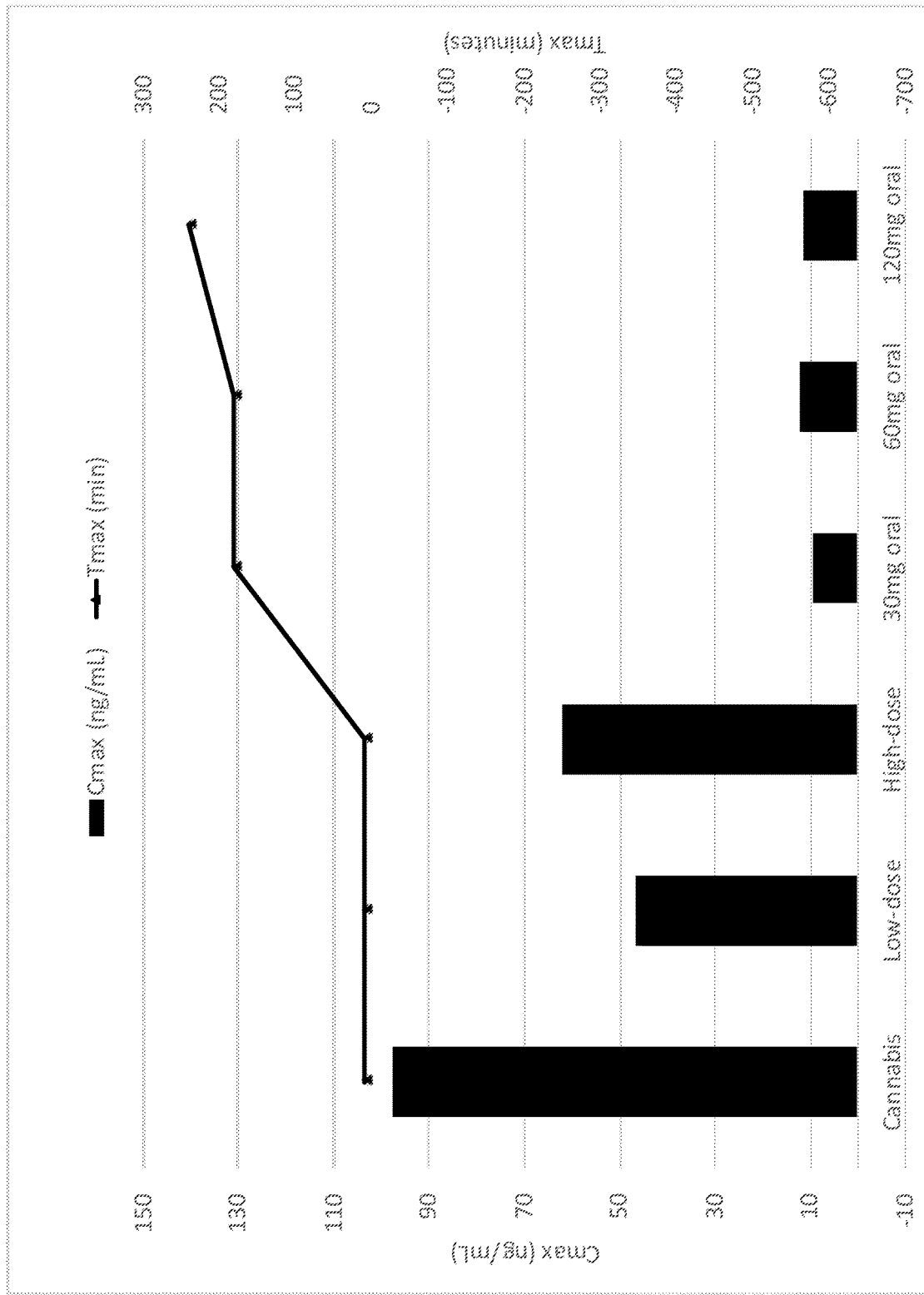
FIG. 5 illustrates the comparison of Cmax and Tmax for six test articles in a blood plasma study.
Figure 6:
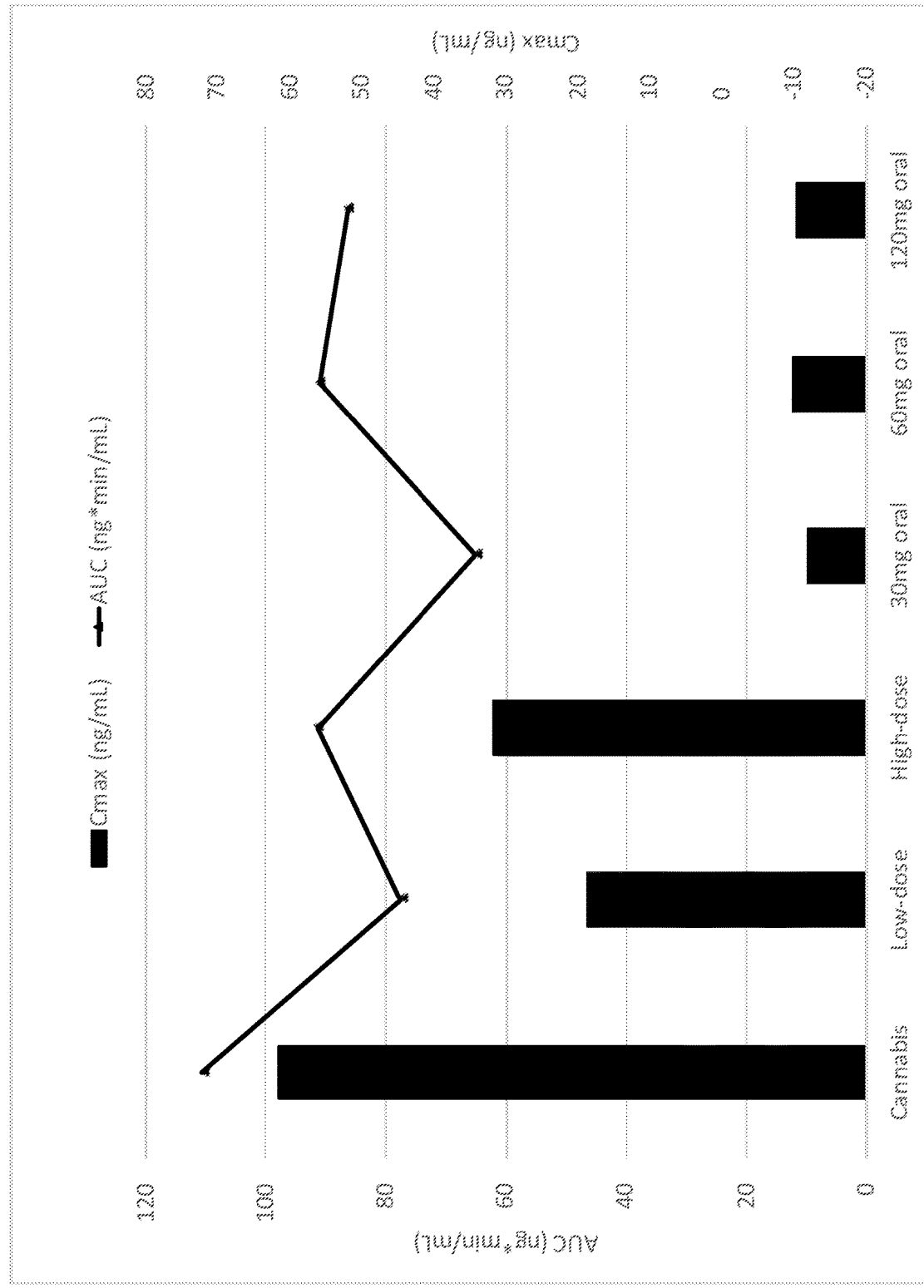
FIG. 6 illustrates the comparison of $C_{max}$ and AUC for six test articles in a blood plasma study.

Comparison of $T_{max}$ and $C_{max}$ of the five blends and reference cannabis cigarette are shown in FIG. 5. Comparison of $C_{max}$ and Area Under the Curve (AUC) of the five blends and reference cigarette are shown in FIG. 6. The data in FIGS. 4-6 show corrected blood cannabinoid concentration values (i.e. apparent blood cannabinoid concentration at each time point minus baseline cannabinoid concentration of the same sample).

Although the $T_{max}$ and $C_{max}$ values are comparable between the tested blends and the reference cannabis cigarette, the rates of cannabinoid absorption within the first 90 seconds differed among the test articles. Some blends showed markedly higher rates of absorption within the first 90 seconds compared to the other blends and with the reference cannabis cigarette. These blends contain cannabinoids that performed well in the Satisfaction Study of Example 3. Moreover, different concentrations of cannabinoid formulations had comparable rates of absorption, suggesting that a lower concentration of cannabinoid may not adversely impact the rate of absorption.

Example 9

Blood Plasma Testing

Blood plasma testing is conducted on twenty subjects (n=20). Five test articles are used in this study: one reference cigarette and three blends delivered to a user in an e-cigarette as an aerosol. The operating temperature of the e-cigarette is from about 75° C. to about 325° C., or from about 100° C. to about 300° C. The reference is a traditional cannabis cigarette. Three blends are tested: 15%, 30%, and 45% concentrations. The three blends are liquid formulations prepared according to protocols similar to that described infra and in Example 1.

All subjects consume about 40 mg of the liquid formulation of each tested blend. Puffs are taken ad libitum starting at time=0 and continuing for 10 minutes. Blood plasma testing occurs for at least 120 minutes from the first puff (t=0) Pharmacokinetic data (e.g., $C_{max}$, $T_{max}$, AUC) for cannabinoids in the plasma of users are obtained at various time periods during those 120 minutes, along with rates of cannabinoid absorption within the first 90 seconds for each test article.

Example 10

Blood Plasma Testing

Blood plasma testing is conducted on twenty subjects (n=20). Several test articles are used in this study: one reference cannabis cigarette and several blends delivered to a user in an e-cigarette as an aerosol. The reference is a traditional cannabis cigarette. The operating temperature of the e-cigarette is from about 75° C. to about 325° C., or from about 100° C. to about 300° C. Various blends and concentrations are tested: 15%, 30%, 45%, etc. The blends are liquid formulations prepared according to protocols similar to that described infra and in Example 1.

All subjects consume about 40 mg of the liquid formulation of each tested blend. Puffs are taken ad libitum starting at time=0 and continuing for. 10 minutes. Blood plasma testing occurs for at least 120 minutes from the first puff (t=0). Pharmacokinetic data (e.g., $C_{max}$, $T_{max}$, AUC) for cannabinoids in the plasma of users are obtained at various time periods during those 120 minutes, along with rates of cannabinoid absorption within the first 90 seconds for each test article.

Example 11

Blood Plasma Testing

Blood plasma testing is conducted on twenty subjects (n=20). Several test articles are used in this study: one reference cannabis cigarette and several blends delivered to a user in an e-cigarette as an aerosol. The reference is a traditional cannabis cigarette. The operating temperature of the e-cigarette is from about 75° C. to about 325° C., or from about 100° C. to about 300° C. Various blends and concentrations are tested: 15%, 30%, 45%, etc. The blends are liquid formulations prepared according to protocols similar to that described infra and in Example 1.

All subjects consume about 40 mg of the liquid formulation of each tested blend. Puffs are taken ad libitum starting at time=0 and continuing for. 10 minutes. Blood plasma testing occurs for at least 120 minutes from the first puff (t=0). Pharmacokinetic data (e.g., $C_{max}$, $T_{max}$, AUC) for cannabinoids in the plasma of users are obtained at various time periods during those 120 minutes, along with rates of cannabinoid absorption within the first 90 seconds for each test article.

Example 12

Blood Plasma Testing

Blood plasma testing is conducted on twenty subjects (n=20). Several test articles are used in this study: one reference cigarette and several blends delivered to a user in an e-cigarette as an aerosol. The reference is a traditional cannabis cigarette. The operating temperature of the e-cigarette is from about 75° C. to about 325° C., or from about 100° C. to about 300° C. Various blends are tested: 15%, 30%, 45%, etc. The blends are liquid formulations prepared according to protocols similar to that described infra and in Example 1.

All subjects consume about 40 mg of the liquid formulation of each tested blend. Puffs are taken ad libitum starting at time=0 and continuing for 10 minutes. Blood plasma testing occurs for at least 120 minutes from the first puff (t=0). Pharmacokinetic data (e.g., $C_{max}$, $T_{max}$, AUC) for cannabinoids in the plasma of users are obtained at various time periods during those 120 minutes, along with rates of cannabinoid absorption within the first 90 seconds for each test article.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following embodiments define the scope of the invention and that methods and structures within the scope of these embodiments and their equivalents be covered thereby.

What is claimed is:

1. A cannabinoid formulation comprising:
  (a) two or more synthetic cannabinoids;
  (b) a solvent, wherein the solvent comprises methane, ethane, propane, butane, pentane, hexane, heptane, octane, nonane, decane, undecane, dodecane, tridecane, tetradecane, pentadecane, hexadecane, heptadecane, octadecane, nonadecane, or eicosane; and
  (c) a biologically acceptable liquid carrier comprising 40-90% propylene glycol and 10-60% glycerin (w/w) wherein the amount of propylene glycol exceeds the amount of glycerin (w/w) wherein
  the stoichiometric ratios of cannabinoid to solvent are about 1:5 to about 5:64.

2. The formulation of claim 1, wherein the one or more cannabinoids are extracted cannabinoids.

3. The formulation of claim 1, wherein the one or more cannabinoids have a purity of greater than about 80% pure, greater than about 85% pure, greater than about 90% pure, greater than about 95% pure, or greater than about 99% pure.

4. The formulation of claim 1, wherein the liquid carrier comprises:
  55% propylene glycol and 45% (w/w) vegetable glycerin,
  60% propylene glycol and 40% (w/w) vegetable glycerin,
  65% propylene glycol and 35% (w/w) vegetable glycerin,
  70% propylene glycol and 30% (w/w) vegetable glycerin,
  75% propylene glycol and 25% (w/w) vegetable glycerin
  80% propylene glycol and 20% (w/w) vegetable glycerin,
  85% propylene glycol and 15% (w/w) vegetable glycerin, or
  90% propylene glycol and 10% (w/w) vegetable glycerin.

5. The formulation of claim 1, wherein the organic solvent is characterized by a melting point <55° C. and a boiling point >−165° C. and at least a 15-degree difference between the melting point and the boiling point.

6. The formulation of claim 1, wherein the organic solvent is characterized by vapor pressure <25 bar at 50° C.

7. The formulation of claim 1, further comprising one or more flavorants.

8. The formulation of claim 1, wherein the stoichiometric ratios of cannabis to organic solvent are about 1:5, 1:6, 1:7, 1:8, 1:9, 1:10, about 1:11, about 1:12, about 1:13, about 2:21, about 2:23, about 2:25, about 3:31, about 3:32, about 3:34, about 3:35, about 3:37, about 3:38, about 4:41, about 4:42, about 4:43, about 4:45, about 4:46, about 4:47, about 4:49, about 4:50, 5:51, 5:52, 5:53, 5:54, 5:56, 5:57, 5:58, 5:59, 5:61, 5:62, 5:63, or 5:64.

9. An electronic cigarette for delivering an inhalable aerosol comprising:
a fluid storage compartment,
the formulation of claim 1 disposed within the fluid storage compartment,
an atomizer comprising a heating element;
a battery, and
a mouthpiece.

10. The electronic cigarette of claim 9, wherein the heater has an operating temperature of about 200° C.

11. A cartomizer for an electronic cigarette, comprising the cannabinoid formulation of claim 1, a fluid storage compartment, and an atomizer comprising a heating element in fluid communication with the formulation.

12. A cartridge for use in an electronic cigarette comprising a fluid storage compartment containing the formulation of claim 1.

13. A kit comprising:
(a) an electronic cigarette for generating an inhalable aerosol comprising:
  (i) a device body comprising a cartridge receptacle,
  (ii) a cartridge comprising a fluid storage compartment, wherein the fluid storage compartment stores a formulation of claim 1,
  (iii) a heater,
  (iv) a battery, and
  (v) a mouthpiece; and
(b) instructions for using the electronic cigarette to generate an inhalable aerosol.

14. A method for administering cannabinoids to a user, comprising,
providing to the user the formulation of claim 1, wherein the formulation can be heated to generate an inhalable aerosol comprising one or more cannabinoids, and one or more of the cannabinoids are inhaled by the user in the inhalable aerosol.

15. The method of claim 14, wherein the formulation is heated with an electronic cigarette operated at about 200° C.

16. The method of claim 14, wherein the wherein the aerosol comprises a condensate of one or more cannabinoids.

17. The method of claim 14, wherein the condensate comprises particle sizes from about 0.1 microns to about 5 microns, from about 0.1 microns to about 1 or 2 microns, from about 0.1 microns to about 0.7 microns, or from about 0.3 microns to about 0.4 microns.

18. The method of claim 14, wherein the aerosol comprises about 0.5% to about 50% (w/w) cannabinoid.

19. The method of claim 14, wherein the cannabinoid formulation has a cannabinoid concentration of from about 30% (w/w) to about 90% (w/w).

20. The method of claim 14, wherein the biologically acceptable liquid carrier also contains glycerol,-trimethylene glycol, water, or ethanol.

* * * * *